(12) United States Patent
O'Brien

(10) Patent No.: US 6,303,318 B1
(45) Date of Patent: Oct. 16, 2001

(54) METHODS FOR THE EARLY DIAGNOSIS OF OVARIAN CANCER

(75) Inventor: Timothy J. O'Brien, Little Rock, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 0 days.

(21) Appl. No.: 09/039,211

(22) Filed: Mar. 14, 1998

Related U.S. Application Data

(60) Provisional application No. 60/041,404, filed on Mar. 19, 1997.

(51) Int. Cl.$^7$ .................. G01N 33/53; G01N 33/574; C12Q 1/68; C07H 21/04; C07K 14/435
(52) U.S. Cl. .................. 435/7.1; 435/6; 435/7.2; 435/23; 536/23.5; 536/24.31; 530/350
(58) Field of Search .................. 435/6, 7.1, 7.4, 435/23; 536/23.5, 24.31, 23.2; 530/350

(56) References Cited

FOREIGN PATENT DOCUMENTS

0594879A1 * 5/1994 (EP) .

OTHER PUBLICATIONS

Anisowicz et al. Molecular Medicine. 2:624–636, Sep. 1996.*

Nishida et al. Gynecologic Oncology. 56:357–361, Sep. 1996.*

Tanimoto et al. Journal of the Society of Gynecol Investigation. 4: 225A, abstract 577, 1997.*

* cited by examiner

*Primary Examiner*—Carla J. Myers
(74) *Attorney, Agent, or Firm*—Benjamin Aaron Adler

(57) ABSTRACT

New molecular markers for the detection of cancerous tissue. The disclosed nucleic acid primer sets, used in combination with quantitative amplification (PCR) of tissue cDNA, can indicate the presence of specific proteases in a tissue sample. The detected proteases are themselves specifically over expressed in certain cancers, and the presence of their genetic precursors may serve for early detection of associated ovarian and other malignancies, and for the design of interactive therapies for cancer treatment.

5 Claims, 17 Drawing Sheets

1) Normal Ovary  2) Tumor
3) Normal Ovary  4) Tumor

0 : < Mean + 2 SD    1 : > Mean + 2 SD < 4 SD    2 : > Mean + 4 SD

TADG12

1.               .15

VVTAAH̲CVYD̲LYLPK

16               .30

SWTIQVGLVSLLDNP    ↓ indicates the site of insert in TADG12

31               .45    H̲ & D̲ are the conserved regions of
                        Serine protease.
APSHLVEKIVYHSKY 46          57

KPKRLGND̲IALL

```
  1  6     10                      53   57
  __ H CVY D LYL _ _ _ _ _ _ _ _ _ _ D _ _ _
     *                               *
        ↑
  site of 133 bp insert in TADG12
```

0 : < Mean + 2 SD    1 : > Mean + 2 SD < 4 SD    2 : > Mean + 4 SD

METHODS FOR THE EARLY DIAGNOSIS OF OVARIAN CANCER

RELATED APPLICATION

This application claims the benefit of provisional application Ser. No. 60/041,404, filed Mar. 19, 1997.

FIELD OF THE INVENTION

The present invention is in the fields of molecular biology and medicine. More specifically, the present invention is in the field of ovarian and other cancer diagnosis.

BACKGROUND OF THE INVENTION

To date, ovarian cancer remains the number one killer of women with gynecologic malignant hyperplasia. Approximately 75% of women diagnosed with such cancers are already at the high-stage (III and IV) of the disease at their initial diagnosis. During the past 20 years, neither diagnosis nor five year survival have greatly improved for these patients. This is substantially due to the high percentage of high-stage initial detections of the disease. Therefore, the challenge remains to develop new markers to improve early diagnosis, and reduce the percentage of high-stage initial diagnoses.

A good tumor marker useful as an indicator of early disease is needed. Extra-cellular proteases have already been implicated in the growth, spread and metastatic progression of many cancers, thereby implying that some extracellular proteases may be candidates for marker of neoplastic development. This is in part due to the ability of malignant cells not only to grow in situ, but to dissociate from the primary tumor and to invade new surfaces. The ability to disengage from one tissue and re-engage the surface of another tissue is what provides for the morbidity and mortality associated with this disease.

In order for malignant cells to grow, spread or metastasize, they must have the capacity to invade local host tissue, dissociate or shed from the primary tumor, and for metastasis to occur, enter and survive in the bloodstream, implant by invasion into the surface of the target organ and establish an environment conducive for new colony growth (including the induction of angiogenic and growth factors). During this progression, natural tissue barriers have to be degraded including basement membranes and connective tissue. These barriers include collagen, laminin, proteoglycans and extracellular matrix glycoproteins including fibronectin.

Degradation of these natural barriers, both surrounding the primary tumor and at sites of metasttic invasion is believed to be brought about by the action of a matrix of extracellular protease. Proteases have been classified into four families: serine proteases, metallo-proteases, aspartic proteases and cysteine proteases. Many proteases have been shown to be involved in the human disease process and these enzymes are targets for the development of inhibitors as new therapeutic agents.

Certain individual proteases have already been shown to be induced and over expressed in a diverse group of cancers, and as such, are potential candidates for markers useful for early diagnosis and possibly therapeutic intervention. A group of examples are listed below. The list of enzymes encompasses members of the metallo-proteases, serine proteases, and cysteine proteases as shown in Table 1.

TABLE 1

Protease Expression in Various Cancers

| Gastric | Brain | Breast | Ovarian |
|---|---|---|---|
| Serine Proteases | | | |
| uPA | uPA | NES-1 | NES-1 |
| PAI-1 | PAI-1 | uPA | uPA |
| | tPA | | PAI-2 |
| Cysteine Proteases | | | |
| Cathepsin B | Cathepsin L | Cathepsin B | Cathepsin B |
| Cathepsin L | | Cathepsin L | Cathepsin L |
| Metallo-proteases | | | |
| Matrilysin* | Matrilysin | Stromelysin-3 | MMP-2 |
| Collagenase* | Stromelysin | MMP-8 | |
| Stromelysin-1* | Gelatinase BMMP-9 | | |
| | Gelatinase A | | | uPA-Urokinase-type plasminogen activator, tPA - Tissue-type plasminogen activator, PAI-I - Plasminogen activator 0 inhibitors, PAI-2 - Plasminogen activator inhibitors, NES-1 - Normal epithelial cell-specific-1, MMP - Matrix P metallo-protease.
*These metallo-proteases are over expressed in gastrointestinal ulcers.

Significantly there is a good body of evidence supporting the down regulation or inhibition of individual proteases and reduction in invasive capacity or malignancy. In work by Clark et al. inhibition of in vitro growth of human small cell lung cancer was demonstrated using a general serine protease inhibitor. More recently, Torres-Rosedo et al., *Proc. Natl. Acad. Sci. USA*, 90, 7181–7185 (1993). demonstrated an inhibition of tumor cell growth of hepatoma cells using specific antisense inhibitors for the serine protease hepsin gene. Metastatic potential has also been shown to be reduced in a mouse model with melanoma cells by using a synthetic inhibitor (batimastat) of metallo-protease. Powell, et al. *Cancer Research,* 53, 417–422 (1993), presented evidence to confirm that the expression of extracellular proteases in relatively non-invasive tumor cells enhances their malignant progression using a tumor-genic but non-metastatic prostate cell line. Specifically, they demonstrated enhanced metastasis after introducing and expressing the PUMP-1 metallo-protease gene. There is also a body of data to support the notion that expression of cell surface proteases on relatively non-metastatic cell types increases the invasive potential of such cells.

SUMMARY OF THE INVENTION

This invention detects the presence of cancers, especially ovarian cancer, by screening for a plurality of mRNA markers in tissue, which markers are indicative of proteases specifically associated with the surface of 80 percent of ovarian tumors, and other tumors. Specific combinations of proteases are characteristic of particular tumor types as is illustrated below. These proteases are considered to be an integral part of tumor growth and metastasis and therefore, markers indicative of their presence or absenceare useful for the diagnosis of cancer. The invention provides a method for detecting malignant hyperplasia in a biological sample comprising the steps of isolating the proteases or protease mRNA present in the tissue sample;

detecting and identifying specific proteases present in the tissue sample from the group of proteases consisting of Stratum Corneum Chymotrytic Enzyme (SCCE), TADG12, TADG13, TADG14, Hepsin, Punp-1 and Protease M. Preferably further comprising the step of comparing the specific proteases detected to reference information and providing a diagnoses based in part on the identification of specific proteases associated with the biological sample. In a preferred mode the invention allows identification of specific tumors based on the expression of particular proteases, or the absence of specific proteases. Alternatively, the method may comprise the step of comparing the specific proteases detected to reference information and providing a treatment based in part on the identification of specific proteases associated with the biological sample. In a preferred mode, the invention allows selection of a treatment based on the expression of particular proteases or the absence of particular proteases. A protease is identified by isolation of and amplification of protease mRNA. Alternatively, a protease is isolated by an antibody. The biological sample may be tissue, or preferably a bodily fluid or more preferably blood or a blood component.

The invention further provides a method for detecting ovarian malignant hyperplasia in a biological sample comprising the steps of:

isolating the proteases or protease mRNA present in the tissue sample;

detecting and identifying specific proteases present in the tissue sample from the group of proteases consisting of Hepsin, Protease M, Complement factor B, SCCE, Serine proteases indicated at Lanes 2 and 4, FIG. 1 TADG12, TADG13, TADG14, Cysteine protease Cathepsin L, and metalo-protease Pump-1. Preferably this method further comprising the step of comparing the specific proteases detected to reference information and providing a diagnoses based in part on the identification of specific proteases associated with the biological sample. Alternatively, the method may comprise the step of comparing the specific proteases detected to reference information and providing a treatment based in part on the identification of specific proteases associated with the biological sample. A protease is identified by isolation of mRNA, conversion of the isolated mRNA to cDNA and amplification of the converted protease cDNA. Alternatively, a protease is isolated or detected by an antibody. The biological sample may be tissue, or preferably a bodily fluid or more preferably blood or a blood component.

Either of the preceding methods, when directed to isolated mRNA may further include the steps of converting the mRNA to cDNA, combining cDNA amplification reagents with the cDNA converted from the isolated mRNA and a plurality of nucleic acid primers selected from the group consisting of SEQ ID NO: 1 to 27, excluding 18 and 19, selected in combinations shown in Table 2 to amplify specific marker nucleic acids, and analyzing the expression product to detect elevated levels of expression of the marker primers in the tissue sample.

The invention further provides materials for practice of the method in the form of a reagent kit comprising a container and reagents comprising a plurality of PCR primers selected from the group consisting of primers each comprising one or more of SEQ ID No. 1–17; 20–28. Alternatively the kit provides a container and at least one antibody to the specific proteases identified in Table 2.

This invention identifies a panel of surface proteases on ovarian and other tumor cells which are characteristic of this type of cancer, and in various combinations are characteristic of individual tumor types. Such information can provide the basis for diagnostic tests (assays or immunohistochemistry) prognostic evaluation (depending on the display pattern) and therapeutic intervention utilizing either antibodies directed at the proteases, antisense vehicles for down regulation, or protease inhibitors both from established inhibition data and/or for the design of new drugs. Long-term treatment of tumor growth, invasion and metastasis has not succeeded with existing chemotherapeutic agents—most tumors become resistant to drugs after multiple cycles of chemotherapy.

Objects & Advantages

An object of the present invention is a number of nucleic acid sequences that are useful in its practice. These nucleic acid sequences are listed in Table 2. It is anticipated that these nucleic acid sequences be used in mixtures to accomplish the utility of this invention. Features of such mixtures include: Seq. 1 with Seq. 2; Seq. 1 with Seq. 3; Seq. 4 with Seq. 5; Seq. 6 with Seq. 7; and Seq. 8 with Seq. 9. The skilled artisan may be able to develop other nucleic acid sequences and mixtures thereof to accomplish the benefit of this invention, but it is advantageous to have the sequences listed in Table 2 available without undue experimentation.

A primary object of the present invention is a method for detecting the presence of malignant hyperplasia in a tissue sample. It is an advantage of the present invention that it has as a particular object the detection of cancer in ovarian tissue. The cancer is detected by analyzing a biological sample for the presence of markers to proteases that are specific indicators of certain types of cancer cells. This object may be accomplished by isolating mRNA from a sample or by detection of proteins by polyclonal or preferably monoclonal antibodies. When using mRNA detection the method may be carried out by combining the isolated mRNA with reagents to convert to cDNA according to standard methods; treating the converted cDNA with amplification reaction reagents (such as cDNA PCR reaction reagents) in a container along with an appropriate mixture of nucleic acid primers selected from the list in Table 2 or as detailed above; reacting the contents of the container to produce amplification products; and analyzing the amplification products to detect the presence of malignant hyperplasia markers in the sample.

For mRNA, the analyzing step may be accomplished using Northern Blot analysis to detect the presence of malignant hyperplasia markers in the amplification product. Northern Blot analysis is known in the art. The analysis step may be further accomplished by quantitatively detecting the presence of malignant hyperplasia marker in the amplification produce, and comparing the quantity of marker detected against a panel of expected values for known presence or absence in normal and malignant tissue derived using similar primers.

TABLE 2

PCR Primers
All Sequences 5' to 3'

Redundant Primers

Serine Protease (histidine) = S1 SEQ ID NO: 1 TGGGTIGTIACIGCIGCICA(CT)TG
Serine Protease (aspartic acid) = AS1 SEQ ID NO: 2 A(AG)IA(AG)IGCIATITCITTICC
Serine Protease (serine) = AS11 SEQ ID NO: 3 A(AG)IGGICCICCI(CG)(TA)(AG)TCICC
Cysteine Protease - sense SEQ ID NO: 4 CA(AG)GGICA(AG)TG(CT)GGI(TA)(CG)ITG(CT)TGG
Cysteine Protease - antisense SEQ ID NO: 5 TAICCICC(AG)TT(AG)CAICC(CT)TC
Metallo Protease - sense SEQ ID NO: 6 CCI(AC)GITG(TC)GGI(GA)(TA)ICCIGA
Metallo Protease - antisense SEQ ID NO: 7 TT(AG)TGICCIAI(CT)TC(AG)TG Specific Primers Serine Protease (hepsin) = sense SEQ ID NO: 8 TGTCCCGATGGCGAGTGTTT
Serine Protease (hepsin) = antisense SEQ ID NO: 9 CCTGTTGGCCATAGTACTGC
Serine Protease (SCCE) = sense SEQ ID NO: 10 AGATGAATGAGTACACCGTG
Serine Protease (SCCE) = antisense SEQ ID NO: 11 CCAGTAAGTCCTTGTAAACC
Serine Protease (Comp B) = sense SEQ ID NO: 12 AAGGGACACGAGAGCTGTAT
Serine Protease (Comp B) = antisense SEQ ID NO: 13 AAGTGGTAGTTGGAGGAAGC
Serine Protease (Protease M) = sense SEQ ID NO: 20 CTGTGATCCACCCTGACTAT
Serine Protease (Protease M) = antisense SEQ ID NO: 21 CAGGTGGATGTATGCACACT
Serine Protease (TADG12) = sense (Ser10-s) SEQ ID NO: 22 GCGCACTGTGTTTATGAGAT
Serine Protease (TADG12) = antisense (Ser10-as) SEQ ID NO: 23 CTCTTTGGCTTGTACTTGCT
Serine Protease (TADG13) = sense SEQ ID NO: 24 TGAGGGACATCATTATGCAC
Serine Protease (TADG13) = antisense SEQ ID NO: 25 CAAGTTTTCCCCATAATTGG
Serine Protease (TADG14) = sense SEQ ID NO: 26 ACAGTACGCCTGGGAGACCA
Serine Protease (TADG14) = antisense SEQ ID NO: 27 CTGAGACGGTGCAATTCTGG
Cysteine Protease (Cath-L) = sense SEQ ID NO: 14 ATTGGAGAGAGAAAGGCTAC
Cysteine Protease (Cath-L) = antisense SEQ ID NO: 15 CTTGGGATTGTACTTACAGG
Metallo Protease (PUMP1) = sense SEQ ID NO: 16 CTTCCAAAGTGGTCACCTAC
Metallo Protease (PUMP1) = antisense SEQ ID NO: 17 CTAGACTGCTACCATCCGTC

BRIEF DESCRIPTION OF THE DRAWINGS

FIG. 10A shows quantitative PCR of hepsin and internal control β-tubulin. FIG. 10B shows a bar graph of expression of hepsin in 10 normal ovaries and 44 ovarian carcinoma samples.

FIG. 12A is a comparison of quantitative PCR of cDNA from normal ovary and ovarian carcinomas. 12B is a bar graph comparing the ratio of SCCE to β-Tubulin in 10 normal and 44 ovarian carcinoma tissues.

FIG. 17A compares PUMP-1 expression in normal and carcinoma tissues using quantitative PCR with an internal β-tubulin control. FIG. 17B shows the ratio of mRNA expression of PUMP-1 compared to the internal control β-tubulin in 10 normal and 44 ovarian carcinomas.

DETAILED DESCRIPTION OF THE INVENTION

Figure 1:
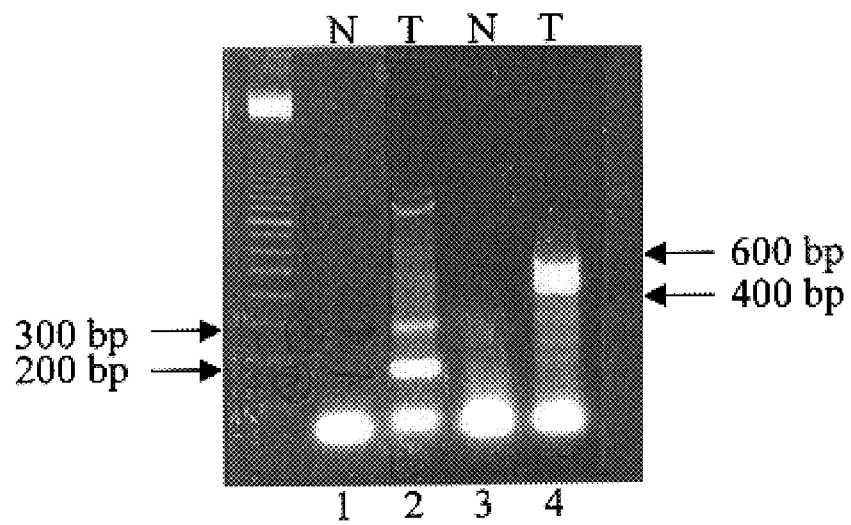
FIG. 1: Serine protease redundant primers: histidine sense (S1) with aspartic acid antisense (AS1), using normal cDNA (Lane 1) and tumor cDNA (Lane 2); and histidine sense (S1) with serine antisense (AS2), using normal cDNA (Lane 3) and tumor cDNA (Lane 4).
Figure 2:
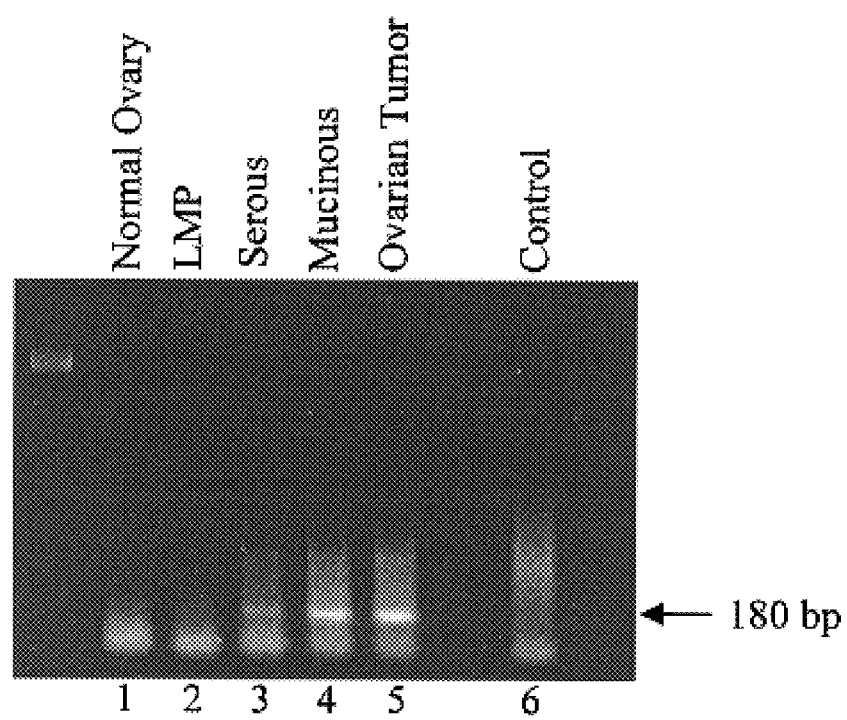
FIG. 2: Cysteine protease redundant primers. Normal (Lane 1), low malignant potential (Lane 2), serious carcinoma (Lane 3), mucinous carcinoma (Lane 4), and clear cell carcinoma (Lane 5).
Figure 3:
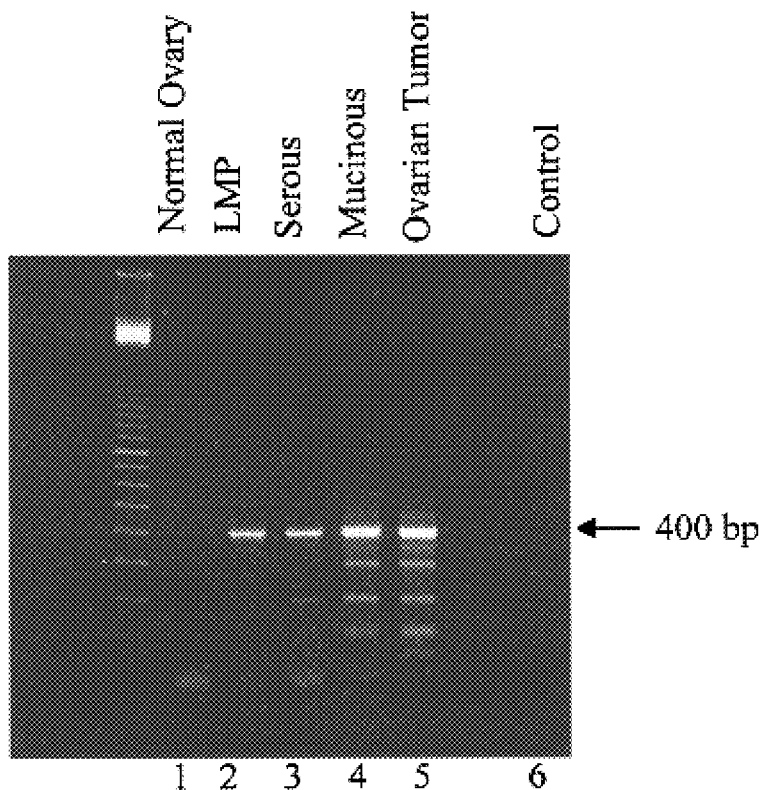
FIG. 3: Metallo-protease redundant primers. Normal (Lane 1), low malignant potential (Lane 2), serious carcinoma (Lane 3), mucinous carcinoma (Lane 4), and clear cell carcinoma (Lane 5).

Based on their unique expression in either low malignant potential tumors or carcinoma, PCR amplified cDNA products were cloned and sequenced and the appropriate gene identified based on nucleotide and amino acid sequences stored in the GCG or EST data bases. FIGS. 1, 2 & 3 show the PCR product displays comparing normal, and carcinomatous tissues using redundant primers for serine proteases (FIG. 1), for cysteine proteases (FIG. 2) and for metalloproteases (FIG. 3). Note the differential expression in the carcinoma tissues versus the normal tissues. The proteases were identified using redundant cDNA primers (see Table 2) to conserved sequences associated with intrinsic enzyme activity (including serine proteases, cysteine proteases and metallo-proteases) by comparing mRNA expression in normal, low malignant potential and overt ovarian carcinoma tissues according to Sakanari et al. *Biochemistry* 86, 4863–4867 (1989).

1. For the serine protease group, using the histidine domain primer sense, S1, in combination with antisense primer AS2, the following proteases were identified:
   (a) Hepsin, a trypsin-like serine protease cloned from hepatoma cells shown to be a cell surface protease essential for the growth of hepatoma cells in culture and highly expressed in hepatoma tumor cells (FIG. 1, Lane 4);
   (b) Complement factor B protease (human factor IX), a protease involved in the coagulation cascade and associated with the production and accumulation of fibrin split products associated with tumor cells (FIG. 1, Lane 4). Compliment factor B belongs in the family of coagulation factors X (Christmas factor), part of the intrinsic pathway, it catalyzes the proteolytic activation of coagulation factor X in the presence of $Ca^{++}$ phospholipid and factor VIIIa e5; and
   (c) A stratum corneum chymotryptic enzyme (SCCE) serine protease involved in desquarnation of skin cells from the human stratum corneum (FIG. 1, Lane 4). It is expressed in keratinocytes of the epidermis and functions to degrade the cohesive structures in the cornified layer to allow continuous skin surface shedding.
2. The cysteine protease group, using redundant sense and anti-sense primers for cysteine proteases, one unique PCR product was identified by over expression in ovarian carcinoma when compared to normal ovarian tissue (FIG. 2, Lanes 3–5). Cloning and sequencing this PCR product identified a sequence of Cathepsin L, which is a lysomal cysteine protease whose expression and secretion is induced by malignant transformation, growth factors and tumor promoters. Many human tumors (including ovarian) express high levels of Cathepsin L. This cysteine protease belongs in the stromolysin family and has potent elastase and collagenase activities. Published data indicates increased levels in the serum of patients with mucinous cystadenocarcinoma of the ovary. It has not heretofore been shown to expressed in other ovarian tumors.
3. Using redundant sense and anti-sense primers for the metallo-protease group, one unique PCR product was detected in the tumor tissue which was absent in normal ovarian tissue (FIG. 3, Lanes 2–5). Subcloning and sequencing of this product indicates it has complete homology with the so-called PUMP-1, (MMP-7) gene in the appropriate region. This zinc binding metallo-protease is expressed as a proenzyme with a signal sequence and is active in gelatin and collagenase digestion. It has also been shown to be induced and over-expressed in 9 of 10 colorectal carcinomas compared to normal colon tissue, suggesting a role for this substrate in the progression of this disease.

The preceding protease entities have all been identified and subcloned from PCR amplification of cDNA derived from serous cystadenocarcinomas. Therefore they are reflective of surface activities for this, the most common form of ovarian cancer. Applicant has also shown PCR amplification bands unique to the mucinous tumor type and the clear cell type of similar base pair size. About 20–25% of ovarian cancers are classified as either mucinous, clear cell, or endometrioid.

Figure 4:
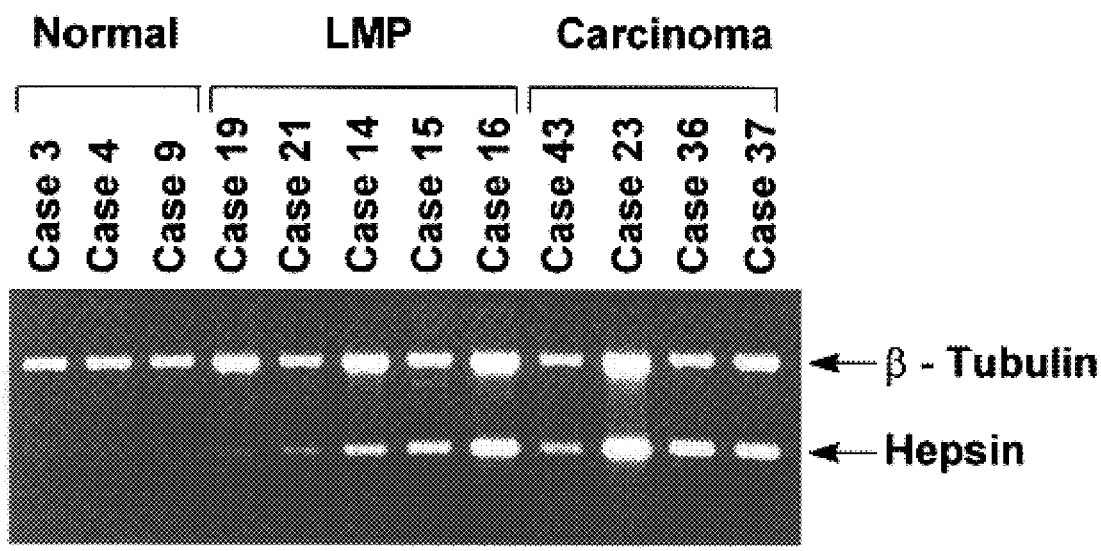
FIG. 4: Specific primers. Serine protease hepsin expression in normal (Lanes 1–3), low malignant potential tumors (Lanes 4–8), and ovarian carcinomas (Lanes 9–12).
Figure 5:
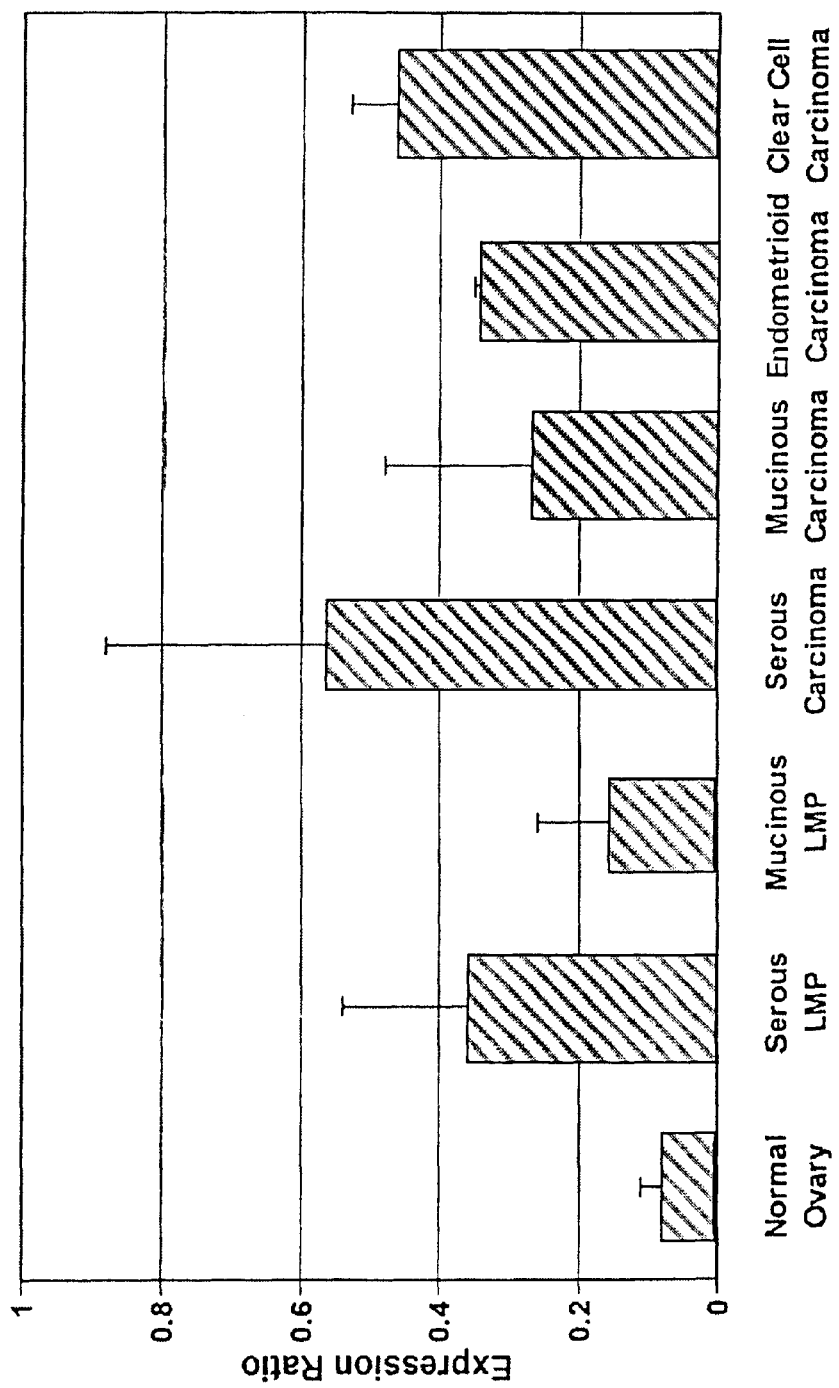
FIG. 5: Hepsin expression levels in normal, low malignant potential tumors, and ovarian carcinomas. S=serious, M=mucinous, LMP=low malignant potential.

The expression of the serine protease hepsin gene in 8 normal, 11 low malignant potential tumors, and 14 carcinoma (both mucinous and serous type) by quantitative PCR using hepsin specific primers was determined (see Table 2) using β-tubulin primers as an internal standard. These data confirm the over expression of the hepsin surface protease gene in ovarian carcinoma, including both low malignant potential tumors and overt carcinoma (Table 3). Expression is increased over normal in low malignant potential tumors and high stage tumors of this group (Stage III) have higher expression when compared to low stage tumors (Stage 1) (Table 4). In overt carcinoma, serous tumors exhibit the highest levels of hepsin expression while mucinous tumors express levels of hepsin comparable with the high stage low malignant potential group (FIGS. 4 & 5).

Figure 6:
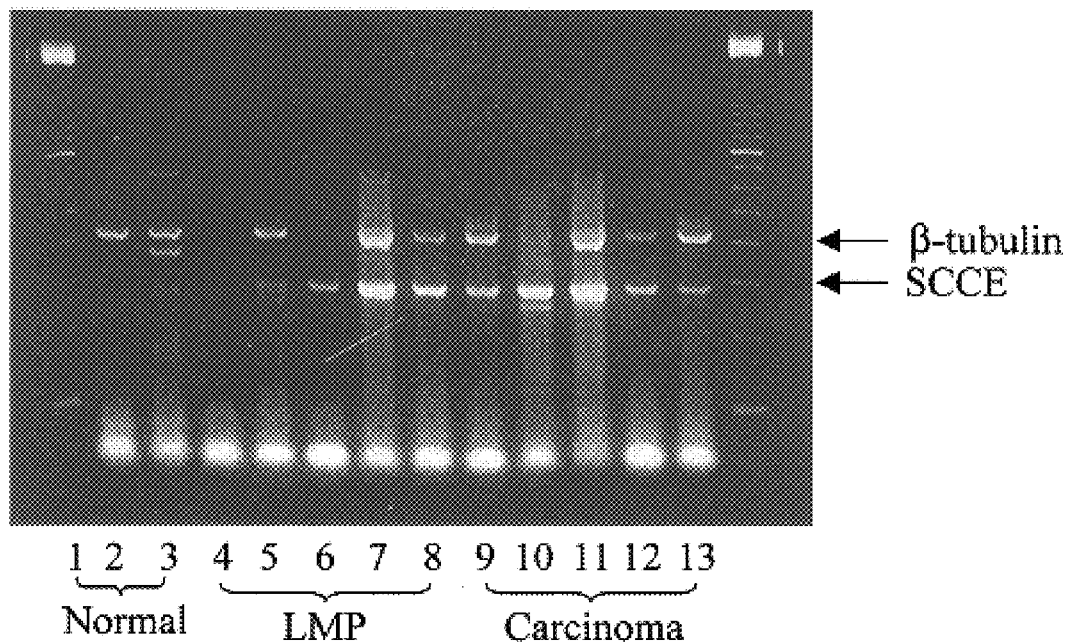
FIG. 6: Serine protease stratum corneum chymotrypsin enzyme (SCCE) expression in normal, low malignant potential tumors, and ovarian carcinomas.
Figure 7:
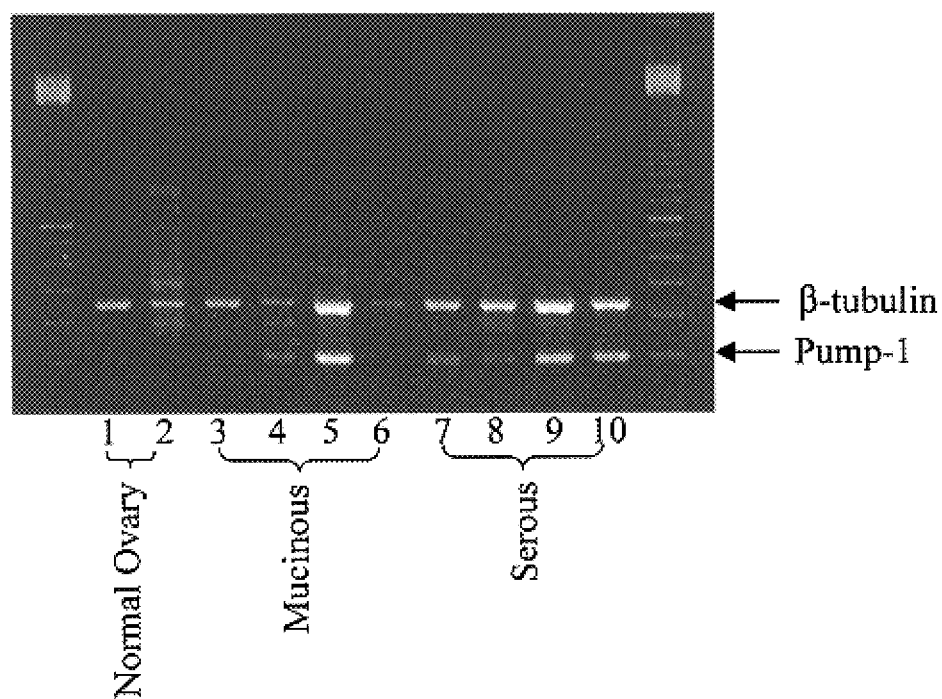
FIG. 7: Metallo-protease PUMP-1 (MMP-7) gene expression in normal (lanes 1–2) and ovarian carcinomas tissue (Lanes 3–10).

Studies using both SCCE specific primers (FIG. 6) and PUMP, specific primers (FIG. 7) indicate over expression of these proteases in ovarian carcinomas.

TABLE 3

Patient Characteristics and Expression of Hepsin Gene

| Case | Histological type | Stage/Grade | LNb mRNA | expression of hepsin |
|---|---|---|---|---|
| 1 | normal ovary | | | n |
| 2 | normal ovary | | | n |
| 3 | normal ovary | | | n |
| 4 | normal ovary | | | n |
| 5 | normal ovary | | | n |
| 6 | normal ovary | | | n |
| | normal ovary | | | n |
| 8 | normal ovary | | | n |
| 9 | normal ovary | | | n |
| 10 | normal ovary | | | n |
| 11 | s adenoma (LMP) | 1/1 | n | + + |
| 12 | s adenoma (LMP) | 1/1 | NE | + + |
| 13 | s adenoma (LMP) | 1/1 | NE | n |
| 14 | s adenoma (LMP) | 1/1 | n | + |
| 15 | s adenoma (LMP) | 3/1 | p | + + |
| 16 | s adenoma (LMP) | 3/1 | p | + + |
| 17 | s adenoma (LMP) | 3/1 | p | + + |
| 18 | m adenoma (LMP) | 1/1 | NE | + + |
| 19 | m adenoma (LMP) | 1/1 | n | n |
| 20 | m adenoma (LMP) | 1/1 | n | n |
| 21 | m adenoma (LMP) | 1/1 | n | n |
| 22 | m adenoma (LMP) | 1/1 | NE | n |
| 23 | s carcinoma | 1/2 | n | + + |
| 24 | s carcinoma | 1/3 | n | + + |
| 25 | s carcinoma | 3/1 | NE | + |
| 26 | s carcinoma | 3/2 | NE | + + |
| 27 | s carcinoma | 3/2 | p | + + |
| 28 | s carcinoma | 3/2 | NE | + |
| 29 | s carcinoma | 3/3 | NE | + |
| 30 | s carcinoma | 3/3 | NE | + + |
| 31 | s carcinoma | 3/3 | NE | + + |
| 32 | s carcinoma | 3/3 | NE | + + |
| 33 | s carcinoma | 3/3 | n | + + |
| 34 | s carcinoma | 3/3 | NE | n |
| 35 | s carcinoma | 3/3 | NE | + + |
| 36 | s carcinoma | 3/3 | NE | + + |
| 37 | s carcinoma | 3/3 | NE | + + |
| 38 | s carcinoma | 3/3 | n | + + |
| 39 | s carcinoma | 3/2 | NE | + |
| 40 | s carcinoma | 3/3 | NE | + + |

TABLE 3-continued

Patient Characteristics and Expression of Hepsin Gene

| Case | Histological type | Stage/Grade | LNb mRNA | expression of hepsin |
|---|---|---|---|---|
| 41 | s carcinoma | 3/2 | NE | + + |
| 42 | m carcinoma | 1/2 | n | n |
| 43 | m carcinoma | 2/2 | NE | + + |
| 44 | m carcinoma | 2/2 | n | + + |
| 45 | m carcinoma | 3/1 | NE | n |
| 46 | m carcinoma | 3/2 | NE | + + |
| 47 | m carcinoma | 3/2 | NE | n |
| 48 | m carcinoma | 3/3 | NE | n |
| 49 | e carcinoma | 2/3 | n | + + |
| 50 | e carcinoma | 3/2 | NE | + + |
| 51 | e carcinoma | 3/3 | NE | + + |
| 52 | c carcinoma | 1/3 | n | + + |
| 53 | c carcinoma | 1/1 | n | + + |
| 54 | c carcinoma | 3/2 | p | + + | a: s; serous, m; mucinous, e; endometrioid, c; clear cell
b: LN; lymph node metastasis, p; positive, n; negative, NE; not examined
c: n; normal range is equal to Mean ±2SD, +; Mean +2SD to +4SD, + +; MEan +4SD or greater

TABLE 4

Over expression of Hepsin in Normal Ovaries and Ovarian Tumors

| TYPE | N | Hepsin over expression | Ratio of Hepsin to β-Tubulin |
|---|---|---|---|
| Normal | 10 | 0 (0%) | 0.06 ± 0.05 |
| LMP | 12 | 7 (58.3%) | 0.26 ± 0.19 |
| Serous | 7 | 6 (85.7%) | 0.34 ± 0.20 |
| Mucinous | 5 | 1 (20.0%) | 0.14 ± 0.12 |
| Carcinomas | 32 | 27 (84.4%) | 0.46 ± 0.29 |
| Serous | 19 | 18 (94.7%) | 0.56 ± 0.32 |
| Mucinous | 7 | 3 (42.9%) | 0.26 ± 0.22 |
| Endometrioid | 3 | 3 (100%) | 0.34 ± 0.01 |
| Clear Cell | 3 | 3 (100%) | 0.45 ± 0.08 |

A tumor tissue bank of fresh frozen tissue of ovarian carcinomas as shown in Table 5 was used for evaluation. Approximately 100 normal ovaries removed for medical reasons other than malignancy were obtained from surgery were available as controls.

TABLE 5

Ovarian Cancer Tissue Bank

| | Total | Stage I/11 | State III/IV | No Stage |
|---|---|---|---|---|
| Serous | | | | |
| Malignant | 166 | 15 | 140 | 8 |
| LMP | 16 | 9 | 7 | 0 |
| Benign | 12 | 0 | 0 | 12 |
| Mucinous | | | | |
| Malignant | 26 | 6 | 14 | 6 |
| LMP | 28 | 25 | 3 | 0 |
| Benign | 3 | 0 | 0 | 3 |
| Endometrioid | | | | |
| Malignant | 38 | 17 | 21 | 0 |
| LMP | 2 | 2 | 0 | 0 |
| Benign | 0 | 0 | 0 | 0 |
| Other* | | | | |
| Malignant | 61 | 23 | 29 | 9 |
| LMP | 0 | 0 | 0 | 0 |
| Benign | 5 | 0 | 0 | 5 |

*Other category includes the following tumor types: Brenner's tumor, thecoma, teratoma, fibrothecoma, fibroma, granulosa cell, clear cell, germ cell, mixed mullerian, stromal, undifferentiated, and dysgerminoma.

From the tumor bank approximately 100 carcinomas were evaluated encompassing most histological sub-types of ovarian carcinoma including borderline or low-malignant potential tumors and overt carcinomas. The approach included using mRNA prepared from fresh frozen tissue (both normal and malignant) to compare expression of genes in normal, low malignant potential tumors and overt carcinomas. The cDNA prepared from poly A plus mRNA was deemed to be genomic DNA free by checking all preparations with primers that encompassed a known intron-exon splice site using both β-tubulin and p53 primers.

Only cDNA preparation deemed free of genomic DNA was used for gene expression analysis. Redundant primers were prepared for serine proteases, metallo-proteases and cysteine protease. The primers were synthesized to consensus sequences of amino acid surrounding the catalytic triad for serine proteases viz. histidine . . . aspartate . . . and serine. Both sense (histidine & aspartate) and antisense redundant primers (aspartate and serine) were synthesized as shown in Table 2 for serine protease redundant primers.

Applicant compared the PCR products amplified from normal and carcinoma cDNAs using sense-histidine and antisense-aspartate as well as sense-histidine and antisense-serine. The anticipated PCR products of approximately 200 bp and 500 bp for those pairs of primers were observed. (Aspartate is approximately 50–70 amino acids down stream from histidine and serine is about 100–150 amino acids toward the carboxy end of proteases from histidine).

Figure 8:
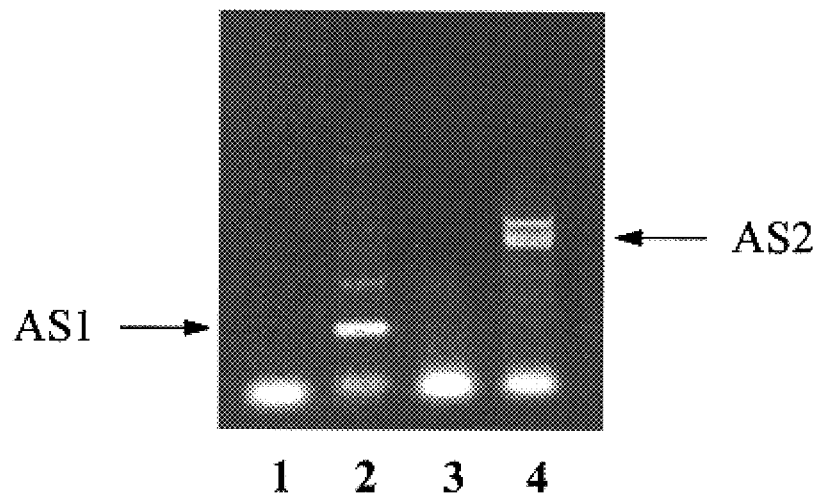
FIG. 8: Agarose gel comparison of PCR products derived from normal and carcinoma cDNA.

FIG. 8 shows a comparison of PCR products derived from normal and carcinoma cDNA as shown by staining in an agarose gel. Two distinct bands in Lane 2 were present in the primer pair sense-His-antisense ASP-(AS1) and multiple bands of about 500 bp are noted in the carcinoma lane for the sense-His antisense-Ser (AS2) primer pairs in Lane 4.

To determine the identity of the PCR products, all the appropriate bands were ligated into Promega Tvector plasmid and the ligation product was used to transform JM109 cells (Promega) grown on selection media. After selection of individual colonies, they were cultured and plasmid DNA isolated by means of the WIZARD MINIPREP™ DNA purification system (Promega). Inserts were sequences using a prism ready reaction dydeoxy terminators, cycle sequencing kit (Applied Biosystems). Residual dye terminators were removed from the completed sequencing reaction using a CENTRISEP SPIN™ column Princeton Separation), an applied Biosystems Model 373 A DNA sequencing system. The results of subcloning and sequencing for the serine protease primers are summarized in Table 4.

TABLE 6

Serine Protease Candidates

| Subclone: | Primer Set: | Gene Candidate: |
|---|---|---|
| 1 | His-serine | Hepsin |
| 2 | His-serine | SCCE |
| 3 | His-serine | Compliment B |
| 4 | His-Asp | Cofactor 1 |
| 5 | His-Asp | TADG-12* |
| 6 | His-Ser | TADG-13* |
| 7 | His-Ser | TADG-14* |
| 8 | His-Ser | Protease M |
| 9 | His-Ser | TADG-15* |

*Indicates Novel Proteases

Most of these proteases were identified from the sense-His . . . antisense-Ser primer pair yielding the 500 bp PCR product (FIG. 8, Lane 4). Some of these enzymes are familiar others are not. The following is a short summary of each. Hepsin is a trypsin-like serine protease cloned from hepatoma cells. It is an extracellular protease (includes a secretion signal sequence) which is anchored in the plasma membrane by its amino terminal domain, thereby exposing its catalytic domain to the extracellular matrix. In has also been shown to be expressed in breast cancer cell lines and peripheral nerve cells. It has never before been associated with ovarian carcinoma. Specific primers for the hepsin gene were synthesized and examined its expression using Northern Blots of fetal tissue and ovarian tissue (both normal and ovarian carcinoma).

Figure 9A:
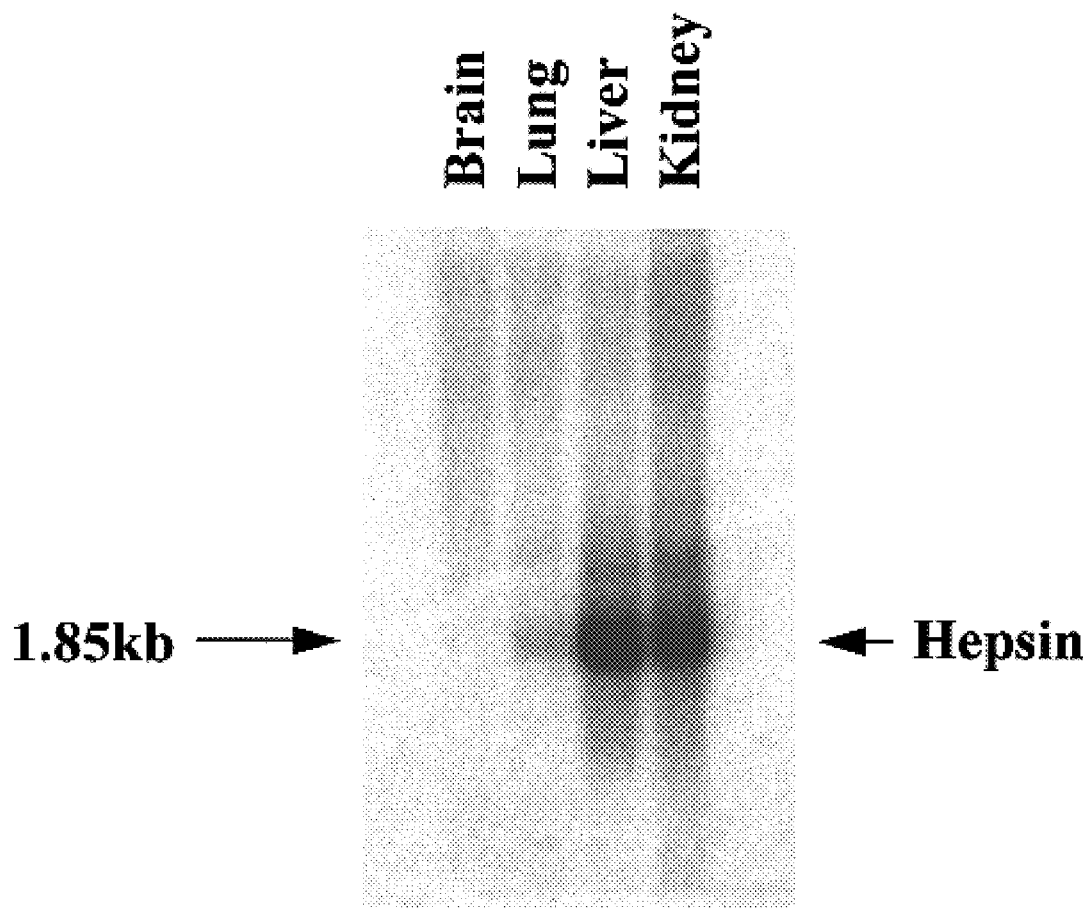
FIGS. 9A & 9B: Northern Blot analysis of hepsin expression in fetal tissue (FIG. 9A) and ovarian tissue (FIG. 9B) using a specific hepsin cDNA probe.
Figure 9B:
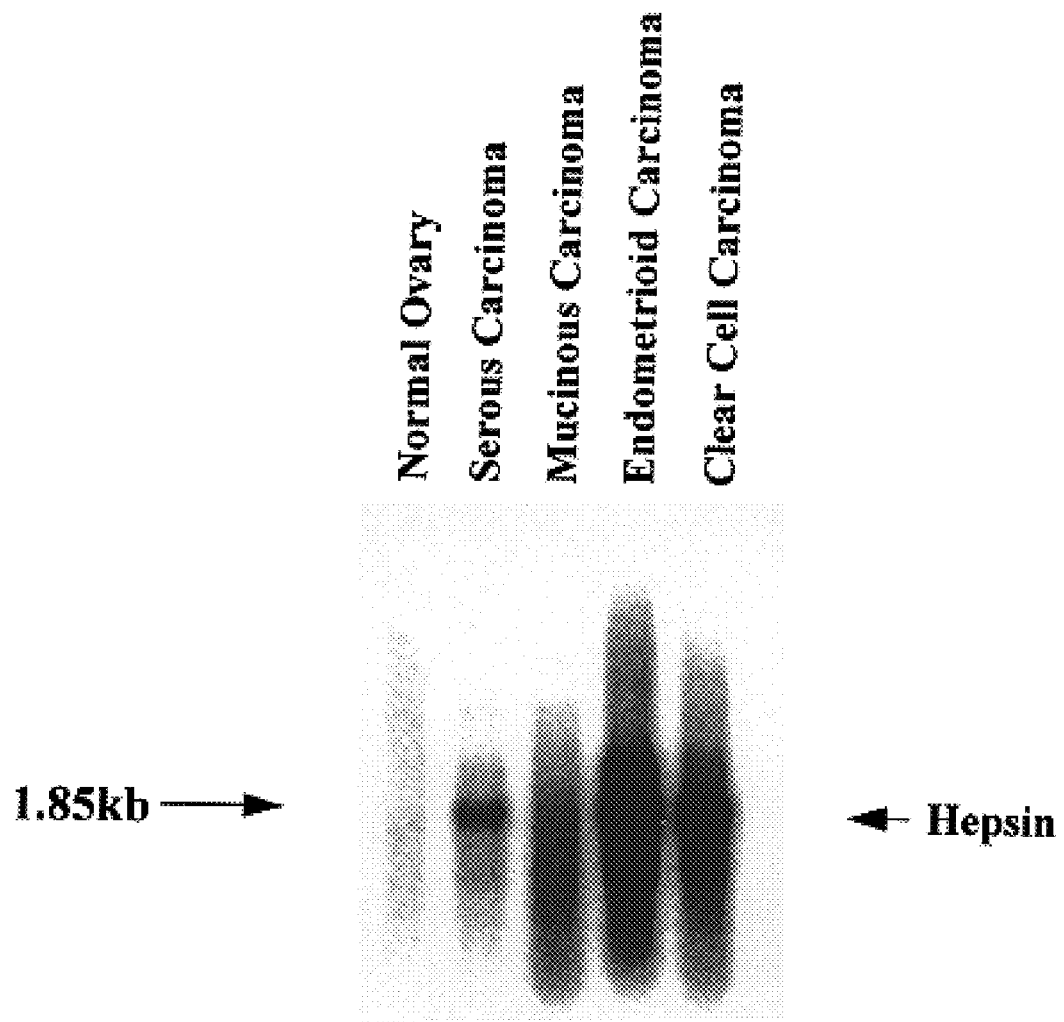

In FIG. 9A, hepsin was expressed in fetal liver and fetal kidney as anticipated, but at very low levels or not at all in fetal brain and lung. In FIG. 9B, hepsin was expressed in ovarian carcinomas of different histologic types, but not in normal ovary. The mRNA identified in both Northerns was the appropriate size for the hepsin transcript. We examined the expression of hepsin in 10 normal ovaries and 44 ovarian tumors using specific primers to β-tubulin and hepsin in a quantitative PCR assay, and found it to be linear over 35 cycles. Expression is presented as the ratio of $p^{32}$ PCR hepsin band to the internal control $p^{32}$ β-tubulin band.

Figure 10A:
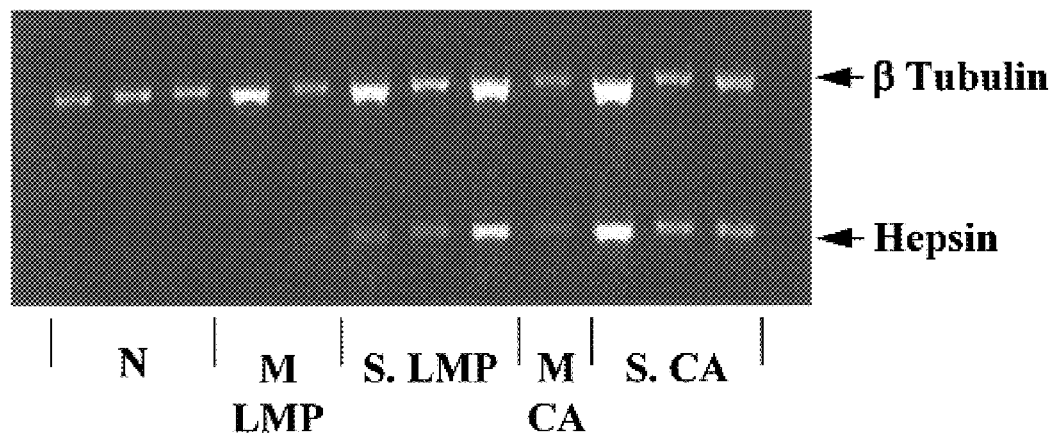
FIGS. 10A & 10B: Hepsin expression in normal (N), mucinous (M) and serous (S) low malignant potential (LMP) tumors and carcinomas (CA).
Figure 10B:
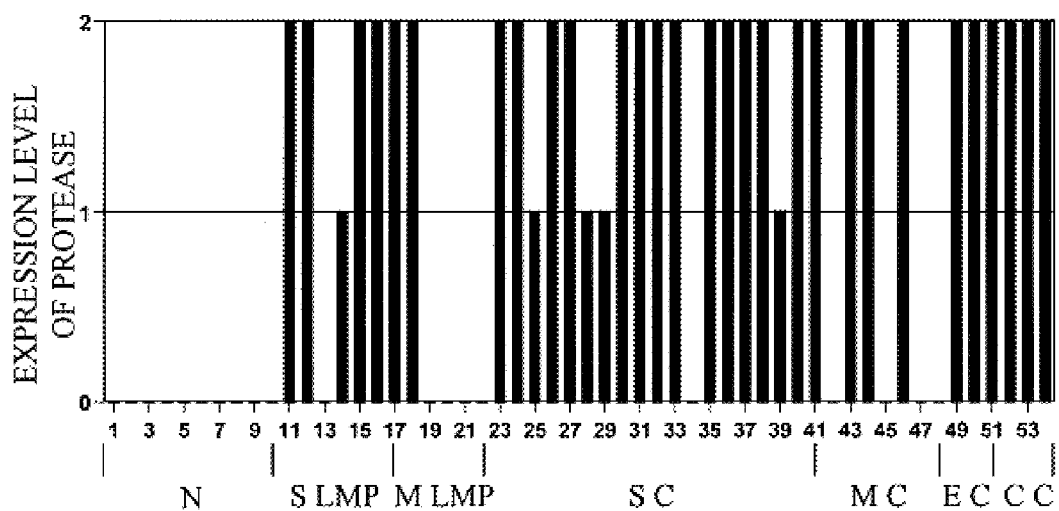

FIGS. 10A & 10B: Hepsin expression in normal (N), mucinous (M) and serous (S) low malignant potential (LMP) tumors and carcinomas (CA). FIG. 10A shows quantitative PCR of hepsin and internal control β-tubulin. FIG. 10B shows a bar graph of expression of hepsin in 10 normal ovaries and 44 ovarian carcinoma samples.

Hepsin mRNA is highly over expressed in most histopathologic types of ovarian carcinomas including some low malignant potential tumors. See FIGS. 10A & 10B. Most noticeably, hepsin is highly expressed in serous, endometrioid and clear cell tumors tested. It is highly expressed in some mucinous tumors but it is not over expressed in the majority of such tumors.

SCCE protease

Stratum corneum chymotrypsin enzyme (SCCE). The PCR product identified was the catalytic domain of the sense-His . . . antisense-Ser of the SCCE enzyme. This extracellular protease was cloned, sequenced and shown to be expressed on surface of keratinocytes in the epidermis. It is a chymotrypsin like serine protease whose function is suggested to be in the catalytic degradation of intercellular cohesive structures in the stratum corneum layer of the skin which allows continuous shedding (desquamation) of cells from the skin surface. Its subcellular localization is in the upper granular layer in the stratum corneum of normal non-palmoplantar skin and in the cohesive parts of hypertrophic plantar stratum corneum. SCCE is exclusively associated with the stratum corneum and has not so far been shown to be expressed in any carcinomatous tissues.

Figure 11A:
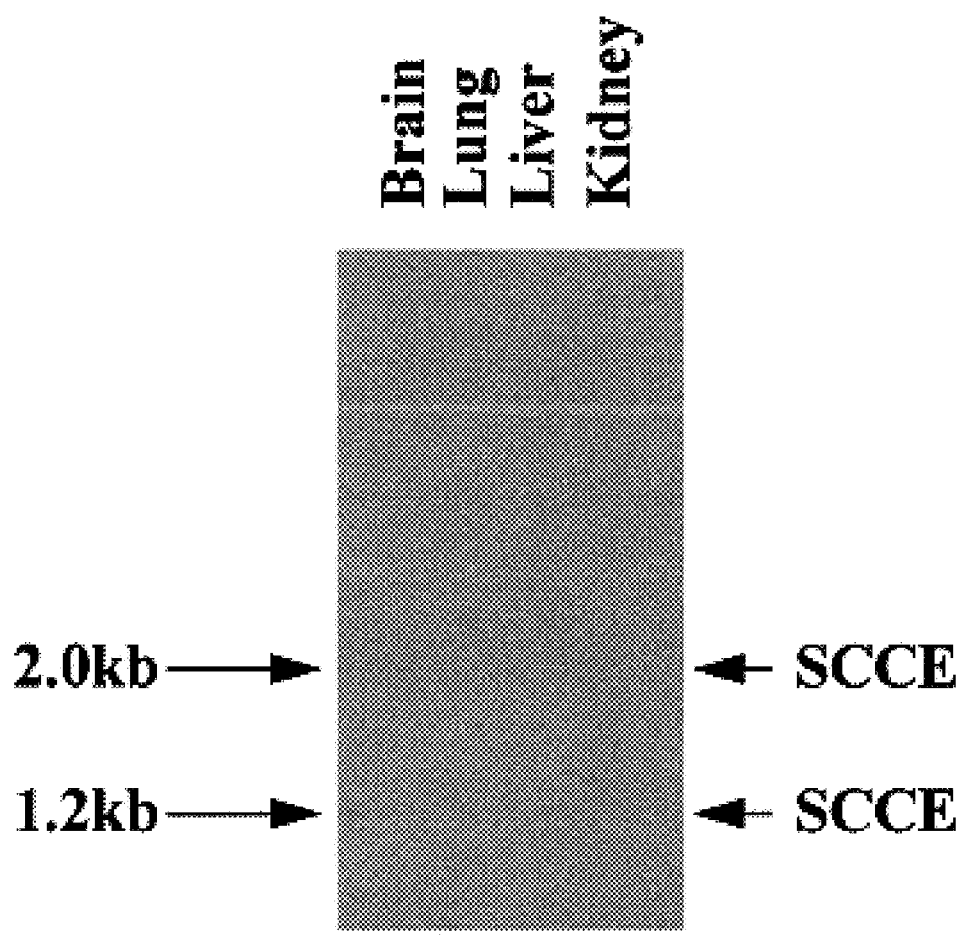
FIGS. 11A & 11B: Northern Blot analysis of mRNA expression of the SCCE gene in fetal tissue (FIG. 11A) and in ovarian tissue (FIG. 11B).
Figure 11B:
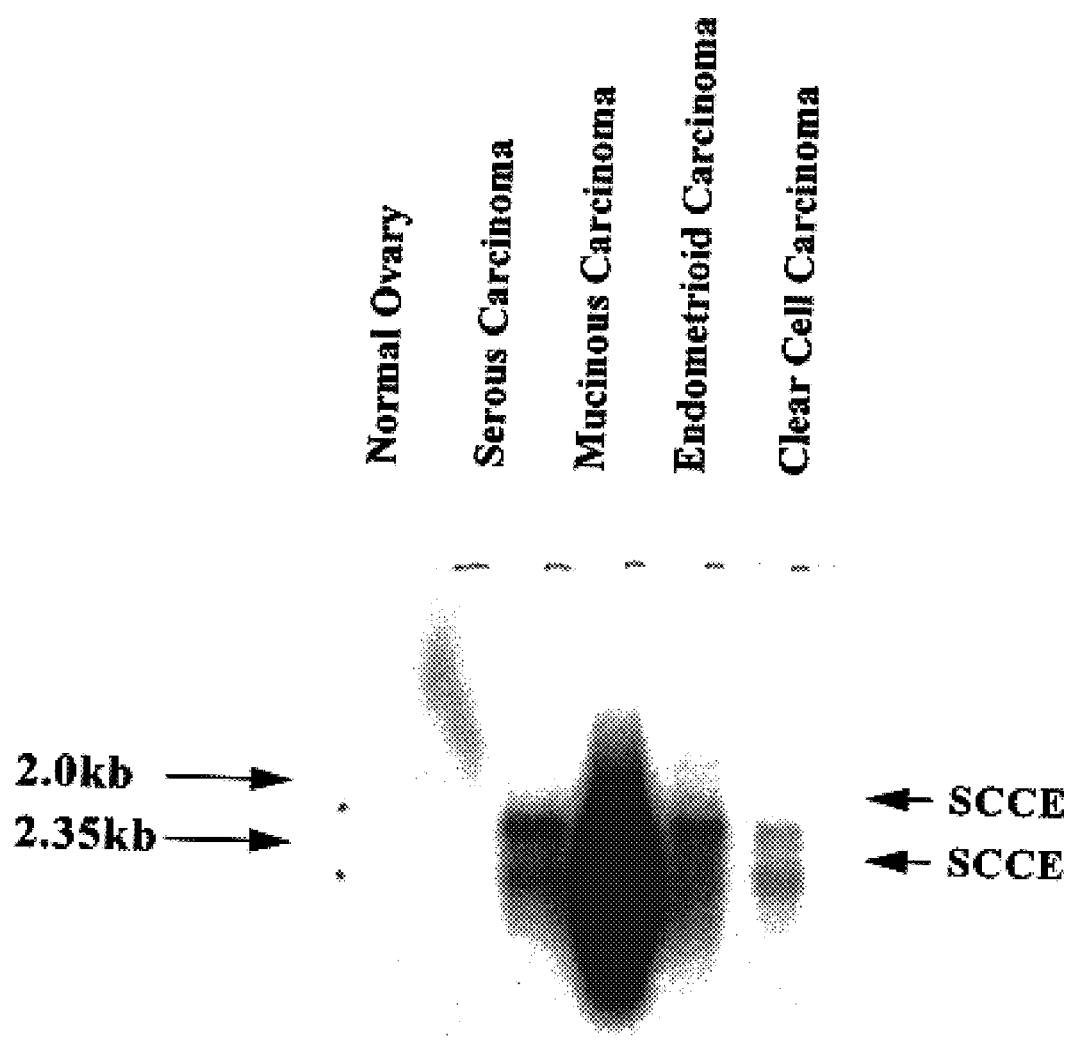

Northern Blots were probed with the PCR product (FIGS. 11A & 11B) to determine expression of SCCE in fetal tissue and ovarian carcinoma. Noticeably messenger detection on the fetal Northern was almost non-existent. A faint band appears in fetal kidney. (This is not a problem with the probe or the blot.) On the other hand, mRNA for SCCE is abundantly obvious in the Northern which includes ovarian carcinoma mRNA (FIG. 11B). Two transcripts of the correct size are observed for SCCE. The same panel of cDNA used for hepsin analysis was used for SCCE expression.

No SCCE expression was detected in the normal ovary lane of the Northern blot. A comparison of all candidate genes including a loading marker (β-tubulin) is shown later to confirm this observation is not a result of a loading bias. Quantitative PCR using SCCE primers with β-tubulin internal control primers confirmed the over expression of SCCE mRNA in carcinoma of the ovary with no expression in normal ovarian tissue (FIG. 12).

Figure 12A:
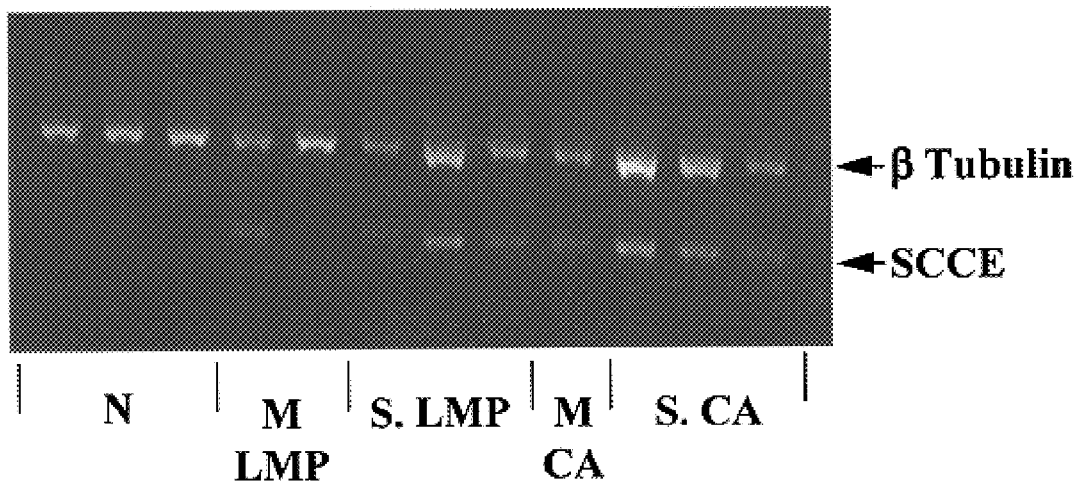
FIGS. 12A & 12B.
Figure 12B:
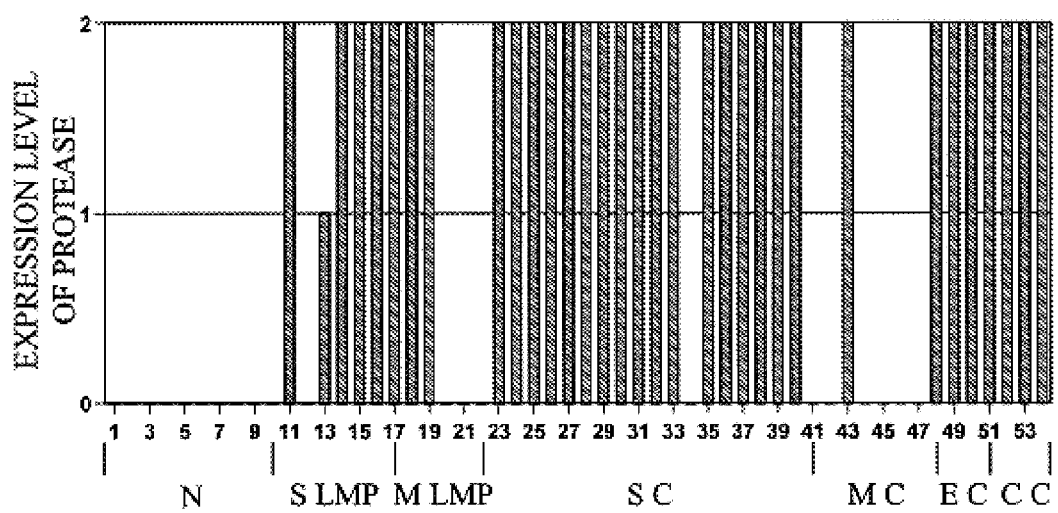

FIGS. 12A & 12B: FIG. 12A is a comparison of quantitative PCR of SCCE cDNA from normal ovary and ovarian carcinomas. FIG. 12B shows the ratio of SCCE to the β-tubulin internal standard in 10 normal and 44 ovarian carcinoma tissues. Again it is observed that mRNA for SCCE is highly over expressed in ovarian carcinoma cells. It is also noted that some mucinous tumors over express SCCE but the majority do not.

Protease M

Figures 13, 14:
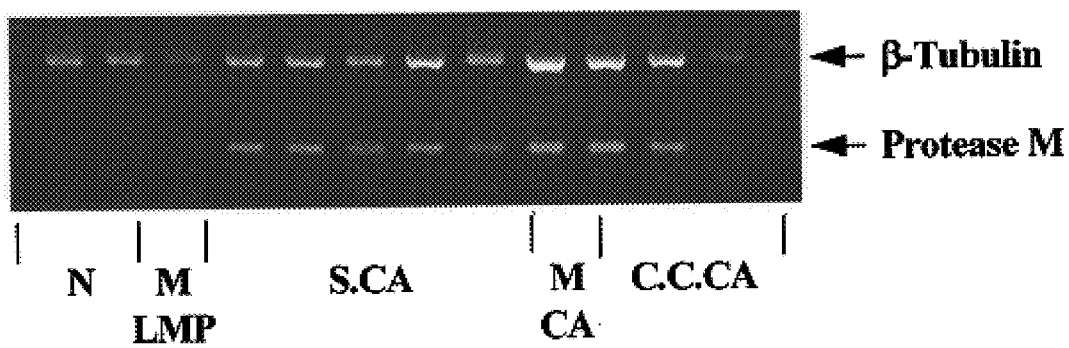
FIG. 13: A comparison by quantitative PCR of normal and ovarian carcinoma expression of mRNA for protease M.
FIG. 14: TADG-12 Catalytic domain of His-Asp including insert near the His 5'-end.

Protease M was identified from subclones of the His-ser primer pair. This protease was first cloned by Anisowicz, et al., *Molecular Medicine*, 2, 624–636 (1996) and shown to be over expressed in breast and ovarian carcinomas. A preliminary evaluation indicates that this enzyme is over expressed in ovarian carcinoma (FIG. 13).

Cofactor I and Complement factor B

Several serine proteases associated with the coagulation pathway have also been subcloned. On exainaion by quantitative PCR of normal and ovarian carcinoma expression of these, it was noticeable that this mRNA was not clearly over expressed in ovarian carcinomas when compared to normal ovarian tissue. It should be noted that the same panel of tumors is used for the evaluation of each candidate protease.

New Previously Unknown Serine Proteases

TADG-12

TADG-12 was identified from the primer pairs sense-His . . . antisense-Asp of FIG. 8, Lane 1 & 2. On subcloning both PCR products in lane two, the 200 bp product had a unique protease-like sequence not included in genbank. It does contain many of the conserved amino acids common for the His-Asp domain of the family of serine proteins. The second larger PCR product (300 bp) was shown to have a high degree of homology with TADG-12 (His-Asp sequence), but also contained approximately 100 bp of unique sequence. Synthesis of specific primers and the sequencing of the subsequent PCR products from three different tumors demonstrated that the larger PCR product (present in about 50% of ovarian carcinomas) includes an insert near the 5' (the histidine) end of the sequence of about 100 bp. This insert may be a retained genomic intron because of the appropriate position of splice sites and the fact that the insert does not contain an open reading frame, see FIG. 14. This suggests the possibility of a splice site mutation, which gives rise to the retention of the intron or a translocation of a sequence into the TADG-12 gene in as many as half of ovarian carcinomas.

TADG-13 and TADG-14

Figure 15A:
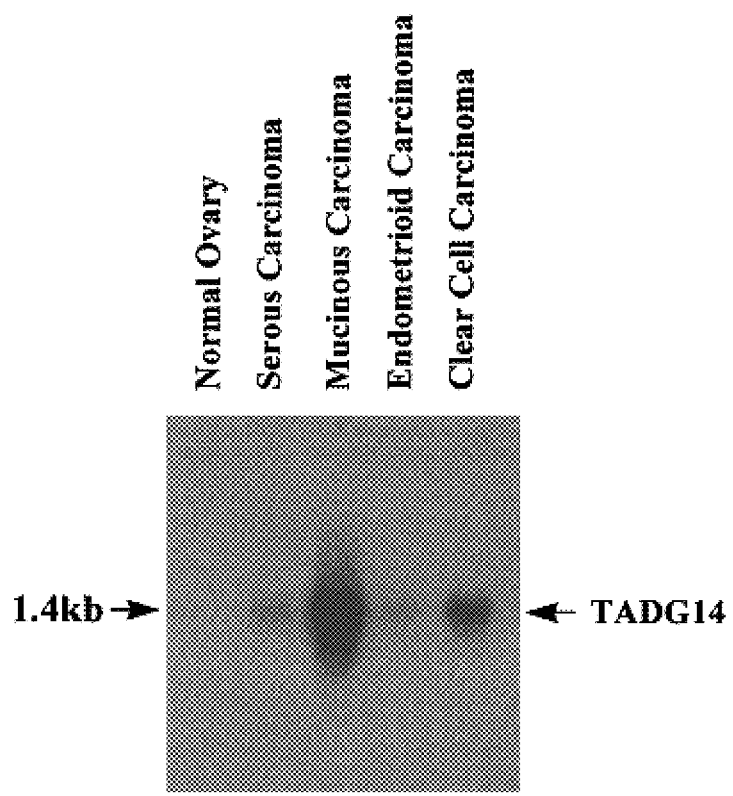
FIGS. 15A & 15B: Northern Blot analysis comparing TADG-14 expression in normal and ovarian carcinoma tissues (FIG. 15A), and preliminary quantitative PCR amplification of normal and carcinoma cDNAs using specific primers for TADG-14 (FIG. 15B).
Figure 15B:
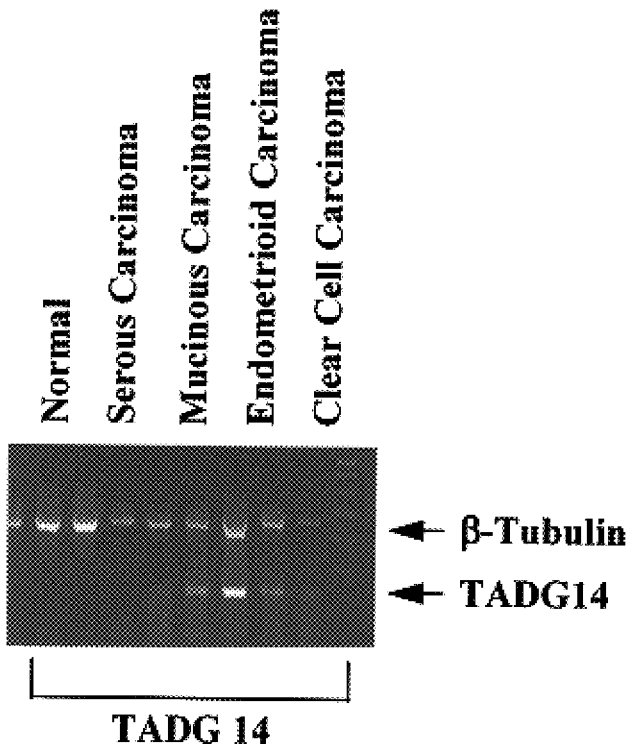

Specific primers were synthesized for TADG-13 and TADG-14 to evaluate expression of genes in normal and ovarian carcinoma tissue. Northern Blot analysis of ovarian tissues indicates the transcript for the TADG-14 gene is approximately 1.4 kb and is expressed in ovarian carcinoma tissues (FIG. 15A) with no noticeable transcript presence in normal tissue. In studies using specific primers in quantitative PCR we noted increased expression of TADG-14 in ovarian carcinoma tissues compared to a normal ovary (FIG. 15B). The presence of a specific PCR product for TADG-14 in both our Hela library and our ovarian carcinoma library has also been confirmed. Some candidate sequences have been screened and isolated from the Hela library for TADG-14. Clearly from sequence homology these genes fit into the family of serine proteases. They are however a heretofore undocumented genes which the specific primers of the invention allow to be evaluated in normal and tumor cells, and the presence or absence of expression of these genes is useful in the diagnosis or treatment selection for specific tumor types. Metallo-proteases.

In a similar strategy using redundant primers to metal binding domains and conserved histidine domains we have identified a differentially expressed PCR product identical to matrix metallo-protease 7 (MMP-7), herein called PUMP-1. Using specific primers for PUMP-1 produced a 250 bp PCR product for Northern Blot analysis.

Figure 16A:
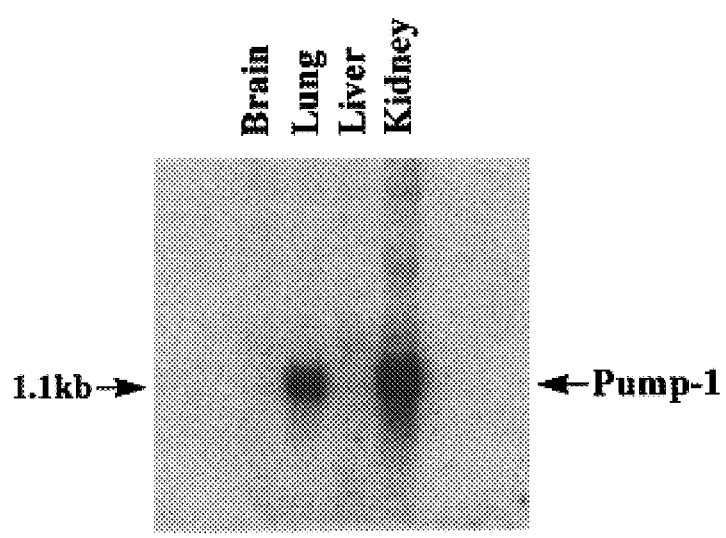
FIGS. 16A & 16B: Northern Blot analysis of the PUMP-1 gene in human fetal tissue (FIG. 16A), and in normal ovary and ovarian carcinomas (FIG. 16B).

MMP-7 or PUMP-1 is differentially expressed in fetal lung and kidney tissues. FIG. 16A shows the expression of PUMP-1 in human fetal tissue and no transcripts could be detected in either fetal brain or fetal liver.

Figure 16B:
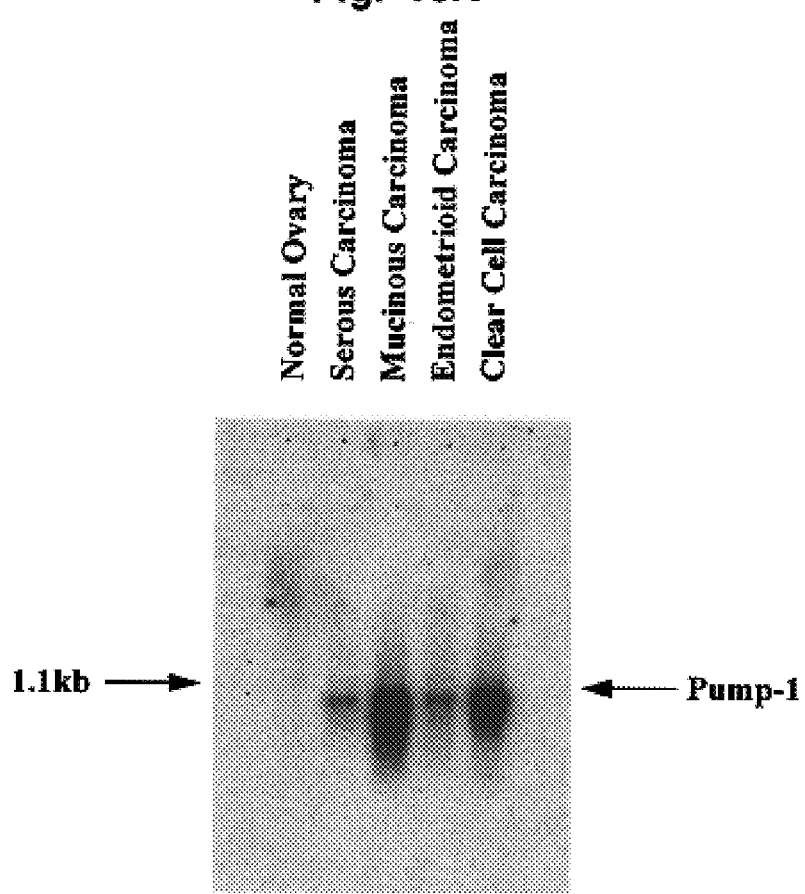
Figure 17A:
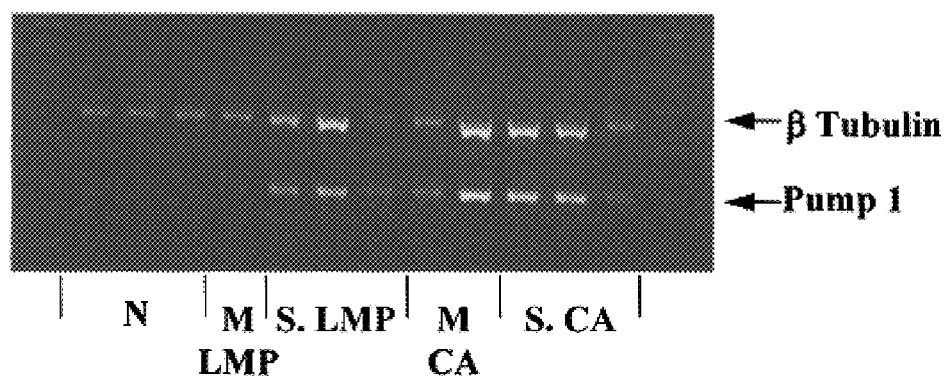
FIGS. 17A & 17B.
Figure 17B:
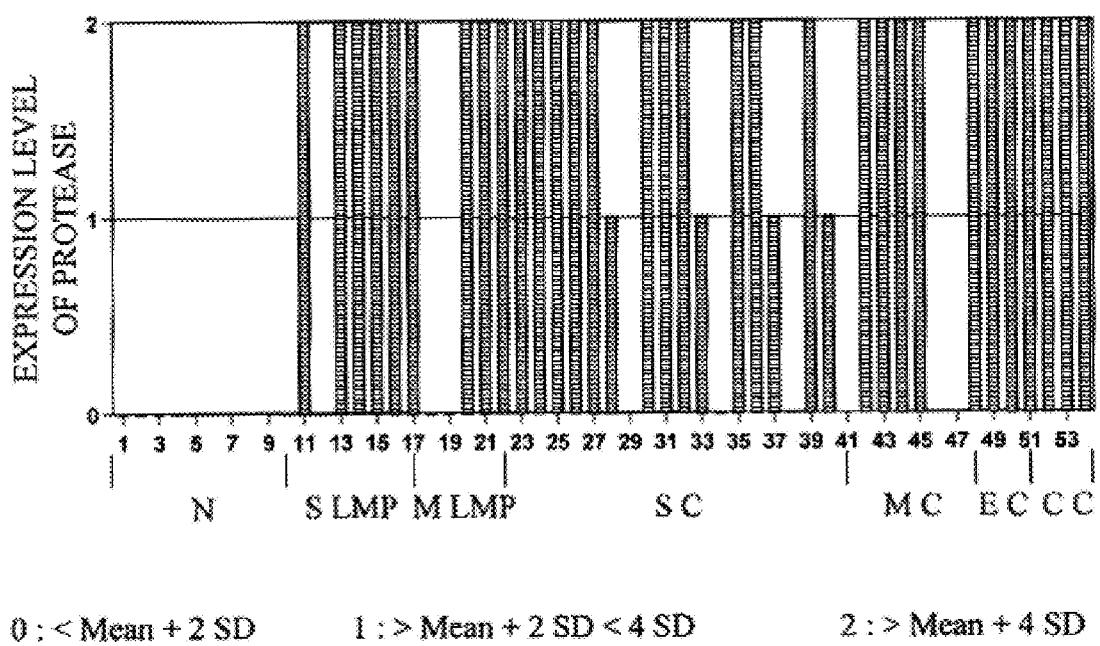

FIG. 16B compares PUMP-1 expression of normal ovary with carcinoma subtype by Northern blot. Notably PUMP-1 is expressed in ovarian carcinoma tissues, again the presence of any transcripts in normal tissue was not detected. Quantitative PCR comparing normal versus ovarian carcinoma expression of the PUMP-1 mRNA indicates that this gene is highly expressed in serous carcinomas including most low malignant serous tumors, and again less frequently expressed in mucinous tumors (see FIGS. 17A & 17B). PUMP-1 however, is so far the protease most frequently found over expressed in mucinous tumors (See Table 7).

Cysteine Proteases

Figure 18:
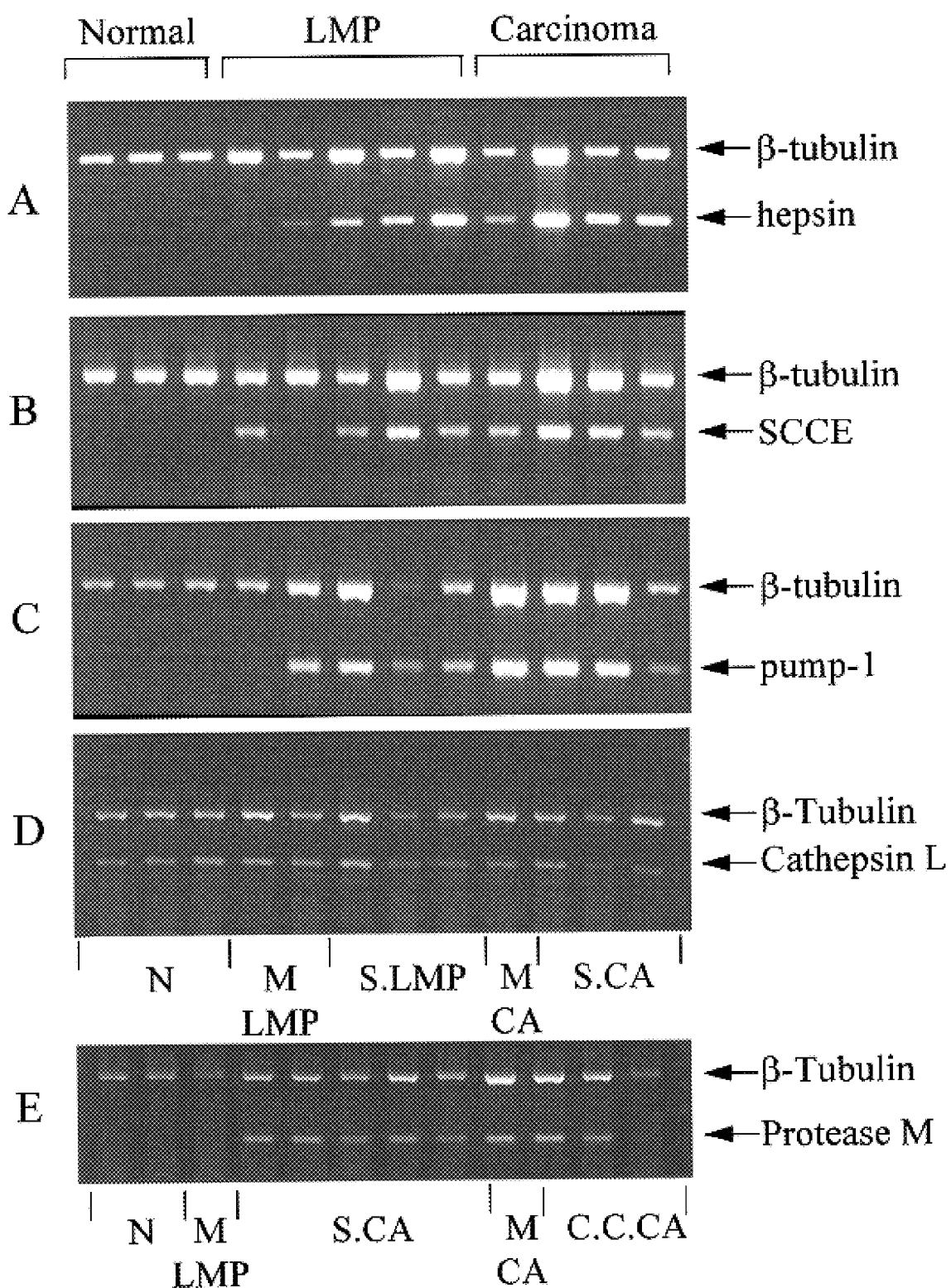
FIG. 18: A comparison of PCR amplified products for the hepsin, SCCE, protease M, PUMP-1 and Cathepsin L genes.

Using redundant cysteine protease primers to conserved domains surrounding individual cysteine and histidine identified the cathepsin-L protease several times from serous carcinomas. An initial examination of the expression of cathepsin L in normal and ovarian tumor tissue indicates that transcripts for this protease are present in both normal and tumor tissues (FIG. 18). However its presence or absence in combination with other proteases of the invention permits identification of specific tumor types and treatment choices.

Summary of Data

Redundant primers to conserved domains of serine, metallo-, and cysteine proteases have yielded a matrix of genes whose mRNAs are over expressed in ovarian carcinoma. The genes which are clearly over expressed include the serine proteases hepsin, SCCE, protease M TADG12, TADG14 and the metallo-protease PUMP-1 (see FIG. 18 and Table 7). Northern Blot analysis of normal and ovarian carcinoma tissues summarized in FIG. 13, indicated over expression of Hepsin, SCCE, PUMP-1 and TADG-14. A β-tubulin probe to examine loading levels was included for comparison.

TABLE 7

Over expression of Proteases in Ovarian Tumors

| Type | N | Hepsin | SCCE | Pump-1 | Protease M |
|---|---|---|---|---|---|
| Normal | 10 | 0% (0/10) | 0% (0/10) | 0% (0/10) | 0% (0/10) |
| LMP | 12 | 58.3% (7/12) | 66.7% (8/12) | 75.9% (9/12) | 75.0% (9/12) |
| serous | 7 | 85.7% (6/7) | 85/7% (6/7) | 85.7% (6/7) | 100% (7/7) |
| mucinous | 5 | 20.0% (1/5) | 40.0% (2/5) | 60.0% (3/5) | 40.0% (2/5) |
| Carcinoma | 32 | 84.4% (27/32) | 78.1% 25/32 | 81.3% (26/32) | 90.6% (29/32) |
| serous | 19 | 94.7% (18/19) | 89.5% (17/19) | 78.9% (15/19) | 94.7% (18/19) |
| mucinous | 7 | 42.9% (3/7) | 28.6% (2/7) | 71.4% (5/7) | 85.7% (6/7) |
| endometrioid | 3 | 100% (3/3) | 100% (3/3) | 100% (3/3) | 100% (3/3) |
| clear cell | 3 | 100% (3/3) | 100% (3/3) | 100% (3/3) | 67.7% (3/3) |

For the most part, these proteins previously have not been associated with the extracellular matrix of ovarian carcinoma cells. No panel of proteases which might contribute to the growth, shedding, invasion and colony development of metastatic carcinoma has been previously described, including the three new candidate serine proteases which are herein disclosed. The establishment of an extracellular protease panel associated with either malignant growth or malignant potential offers the opportunity for the identification of diagnostic or prognostic markers and for therapeutic intervention through inhibition or down regulation of these proteases.

The availability of the instant gene specific primers coding the appropriate region of tumor specific proteases allows the amplification of a specific cDNA probe using Northern and Southern analysis, and their use as markers to detect the presence of the cancer in tissue. The probes also allow more extensive evaluation of the expression of the gene in normal ovary versus low malignant potential tumor, and both high and low stage carcinomas. The evaluation of a panel of fresh frozen tissue from all the carcinoma subtypes (Table 5) has allowed the determination of whether a protease is expressed predominantly in early stage disease or specific carcinoma subtypes. It may also be determined whether its expression is confined to a particular stage in tumor progression and/or is associated with metastatic lesions. Detection of specific combinations of proteases is an identifying characteristic of the specific tumor types and yields valuable information for diagnoses and treatment selection. Particular tumor types may be more accurately diagnosed by the characteristic expression pattern of each specific tumor.

EXAMPLE 1

Quantitative PCR

The mRNA over expression of hepsin was detected and determined using quantitative PCR. Quantitative PCR was performed according to the method of Noonan et al *Proc. Natl. Ad Sci., USA*, 87, 7160–7164 (1990) with some modification as previously reported. Oligonucleotide primers were used for: Hepsin, forward 5'-TGTCCCGATGGCGAGTGTTT-3' (Seq. 8) and reverse 5'-CCTGTTGGCCATAGTACTGC-3' (Seq. 9); and β-tubulin, forward 5'-TGCATTGACAACGAGGC-3' (Seq. 18) and reverse 5'-CTGTCTTGA CATTGTTG-3' (Seq. 19). β-tubulin was utilized as an internal control. The predicted sizes of the amplified genes were 282 bp for hepsin and 454 bp for β-tubulin. The primer sequences used in this study were designed according to the cDNA sequences described by Leytus et al. *Biochemistry,* 27, 1067–1074(1988) for hepsin, and Hall et al *Mol. Cell. Biol.,* 3, 854–862 (1983) for β-tubulin. The PCR reaction mixture consisted of cDNA derived from 50 ηg of mRNA converted by conventional techniques, 5 pmol of sense and antisense primers for both the hepsin gene and the β-tubulin gene, 200 μmol of dNTPs, 5 μCi of $\alpha^{32}$ PdCTP and 0.25 unit of Taq DNA polymerase with reaction buffer (Promega) in a final volume of 25 μl. The target sequences were amplified in parallel with the P-tubulin gene. Thirty cycles of PCR were carried out in a Thermal Cycler (Perkin-Elmer Cetus). Each cycle of PCR included 30 seconds of denaturation at 95° C., 30 seconds of annealing at 63° C. and 30 seconds of extension at 72° C. The PCR products were separated on 2% agarose gels and the radioactivity of each PCR product was determined by using a Phospho Imager™ (Molecular Dynamics). Student's t test was used for comparison of mean values. The other proteases may also be amplified by the same method, selecting the appropriate primers from Table 2.

Northern Blots

Significant information can be obtained by examining the expression of these candidate genes by Northern Blot. Analysis of normal adult multi-tissue blots offers the opportunity to identify normal tissues which may express the protease. Ultimately if strategies for inhibition of proteases for therapeutic intervention are to be developed, it will be essential to appreciate the expression of these genes in normal tissue if it occurs. Significant information from the examination of fetal tissue Northern analysis can be expected. Genes over expressed in carcinomas are often highly expressed in organogenesis. As we have indicated, the hepsin gene cloned from hepatoma cells and over expressed in ovarian carcinoma is overtly expressed in fetal liver. It was also detected in fetal kidney and therefore could be a candidate for expression in renal carcinomas.

Northern panels for examining expression of protease genes in a multi-tissue normal adult Northern as well as fetal tissue Northern are commercially available (Clontech). Such evaluation tools are not only important to confirm the over expression of individual transcripts in tumor versus normal but also provides the opportunity to confirm transcript size, and to determine if alternate splicing or other transcript alteration may occur in ovarian carcinoma.

EXAMPLE 2

Northern Blot Analysis

Northern blot analysis was performed as follows:

10 μg of mRNA was loaded onto a 1% formaldehyde-agarose gel, electrophoresed and blotted on a HyBond-N+™ nylon membrane (Amersham). $^{32}$P-labeled cDNA probes were made using Prime-a-Gene Labeling System™ (Promega). The PCR products amplified by specific primers were used for probes.

Blots were pre-hybridized for 30 min and hybridized for 60 min at 68° C. with $^{32}$P-labeled cDNA probe in ExpressHyb™ Hybridization Solution (CLONTECH). Control hybridization to determine relative gel loading was accomplished using the β-tubulin probe.

Cloning & Characterization

Cloning and characterization of new gene candidates was undertaken to expand the panel representative of extracellular proteases specific for ovarian carcinoma subtypes. Sequencing of the PCR products derived from tumor cDNA confirms the potential candidacy of these genes. These three genes all have conserved residues within the catalytic triad sequence consistent with their membership in the serine protease family. Experiments comparing PCR amplification in normal ovary and ovarian carcinoma suggested over expression and/or alteration in mRNA transcript in tumor tissues.

Figure 19:
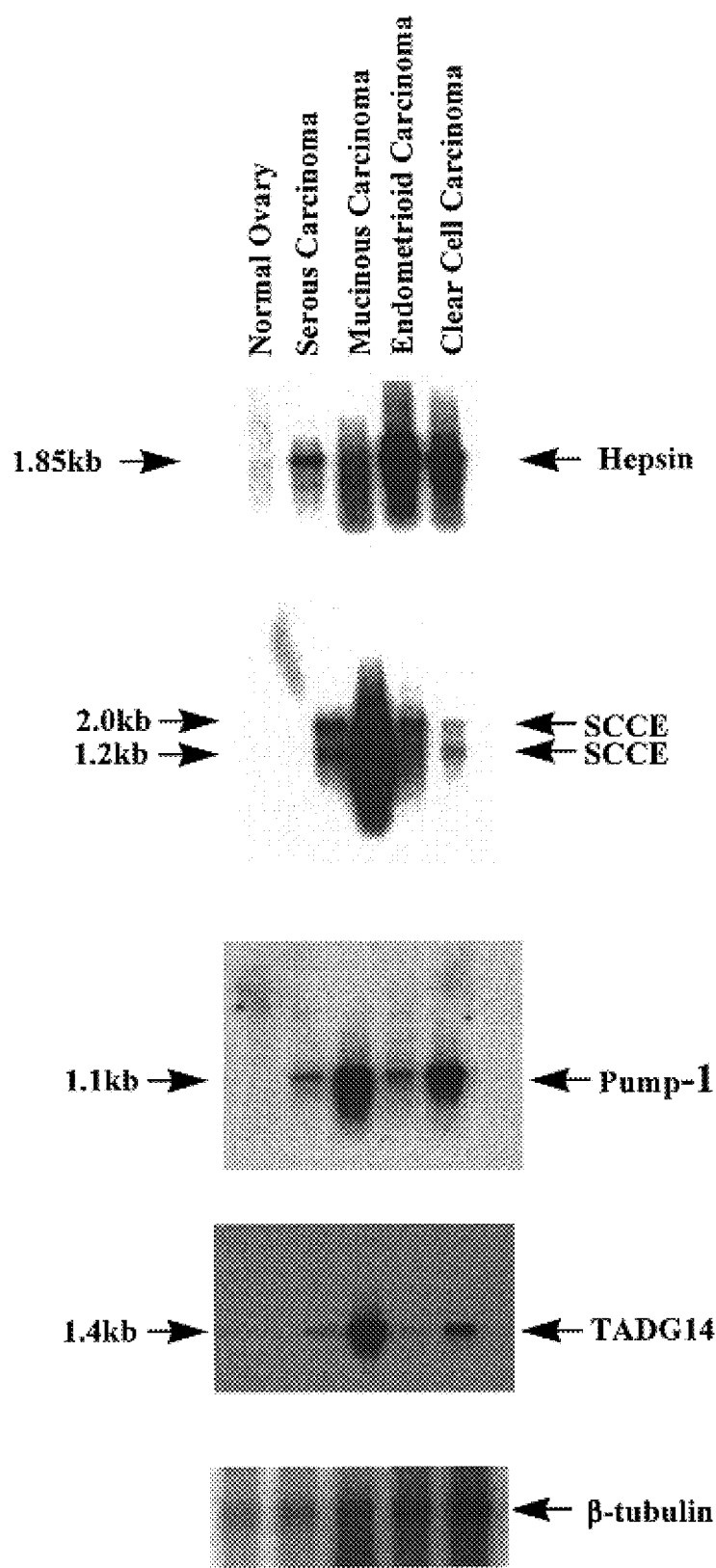
FIG. 19: Northern Blot analysis of ovarian tumors using hepsin, SCCE, PUMP-1, TADG-14 and β-tubulin probes.

Northern blot analysis of TADG-14 confirms a transcript size of 1.4 kb and data indicate over expression in ovarian carcinoma (FIG. 19). Isolation and purification using both PCR and a specific 250 bp PCR product to screen positive plaques yielded a 1.2 kb clone of TADG-14.

While the above description contains many specifics, these should not be construed as limitations on the scope of the invention, but rather as exemplifications of one or another preferred embodiment thereof. Many other variations are possible, which would be obvious to one skilled in the art. Accordingly, the scope of the invention should be determined by the scope of the appended claims and their equivalents, and not just by the embodiments.

I claim:

1. A method for detecting ovarian malignant hyperplasia in a biological sample comprising the steps of:
   isolating proteases present in said sample;
   detecting and identifying specific proteases present in said sample wherein said proteases are selected from the group consisting of Stratum Corneum Chymotrytic Enzyme (SCCE), Hepsin, and metallo-protease Pump-1, wherein an increase in the quantity of said proteases in said sample versus a control sample is indicative of the presence of ovarian malignant hyperplasia.

2. The method according to claim 1 wherein the protease is isolated by an antibody.

3. The method according to claim 1 wherein the biological sample is tissue.

4. The method according to claim 1 wherein the biological sample is a bodily fluid.

5. The method according to claim 4 wherein the biological sample is blood.

* * * * *

```
                        SEQUENCE LISTING (1) GENERAL INFORMATION:

(iii) NUMBER OF SEQUENCES:   28

(2) INFORMATION FOR SEQ ID NO:   1:

(i) SEQUENCE CHARACTERISTICS:
            (A) LENGTH:   23 base pairs
            (B) TYPE:  nucleic acid
            (C) STRANDEDNESS:   double
            (D) TOPOLOGY:   linear (ii) MOLECULE TYPE:
            (A) DESCRIPTION:   cDNA to mRNA (iii) HYPOTHETICAL:   no (iv) ANTI-SENSE:   no (ix) FEATURE:
```

(D) OTHER INFORMATION: N = other = inosine
                    for bases 6, 9, 12, 15, and 18

(xi) SEQUENCE DESCRIPTION: SEQ ID NO:    1:

TGGGTNGTNA CNGCNGCNCA YGT                                               23

(2) INFORMATION FOR SEQ ID NO: 2:

(i) SEQUENCE CHARACTERISTICS:
                (A) LENGTH:   20 base pairs
                (B) TYPE:  nucleic acid
                (C) STRANDEDNESS:  double
                (D) TOPOLOGY:  linear (ii) MOLECULE TYPE:
                (A) DESCRIPTION:   cDNA to mRNA (iii) HYPOTHETICAL:  no (iv) ANTI-SENSE:  no (ix) FEATURE:
                (D) OTHER INFORMATION: N = other = inosine
                    for bases 3, 6, 9, 12, 15, and 18

(xi) SEQUENCE DESCRIPTION: SEQ ID NO:    2:

ARNARNGCNA TNTCNTTNCC                                                   20

(2) INFORMATION FOR SEQ ID NO: 3:

(i) SEQUENCE CHARACTERISTICS:
                (A) LENGTH:   20 base pairs
                (B) TYPE:  nucleic acid
                (C) STRANDEDNESS:  double
                (D) TOPOLOGY:  linear (ii) MOLECULE TYPE:
                (A) DESCRIPTION:   cDNA to mRNA (iii) HYPOTHETICAL:  no (iv) ANTI-SENSE:  no (ix) FEATURE:
                (D) OTHER INFORMATION: N = other = inosine
                    for bases 3, 6, 9, 12, and 18

(xi) SEQUENCE DESCRIPTION: SEQ ID NO:    3:

ARNGGNCCNC CNSWRTCNCC                                                   20

(2) INFORMATION FOR SEQ ID NO: 4:

(i) SEQUENCE CHARACTERISTICS:
                (A) LENGTH:   24 base pairs
                (B) TYPE:  nucleic acid
                (C) STRANDEDNESS:  double
                (D) TOPOLOGY:  linear (ii) MOLECULE TYPE:
                (A) DESCRIPTION:   cDNA to mRNA (iii) HYPOTHETICAL:  no (iv) ANTI-SENSE:  no (ix) FEATURE:
                (D) OTHER INFORMATION: N = other = inosine
                    for bases 6, 15, and 18

(xi) SEQUENCE DESCRIPTION: SEQ ID NO:    4:

CARGGNCART GYGGNWSNTG YTGG                                              24

(2) INFORMATION FOR SEQ ID NO: 5:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE:
        (A) DESCRIPTION: cDNA to mRNA (iii) HYPOTHETICAL: no (iv) ANTI-SENSE: yes (ix) FEATURE:
        (D) OTHER INFORMATION: N = other = inosine
            for bases 3, 6, and 15

(xi) SEQUENCE DESCRIPTION: SEQ ID NO: 5:

TANCCNCCRT TRCANCCYTC    20

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE:
        (A) DESCRIPTION: cDNA to mRNA (iii) HYPOTHETICAL: no (iv) ANTI-SENSE: no (ix) FEATURE:
        (D) OTHER INFORMATION: N = other = inosine
            for bases 3, 6, 12, 15, and 18

(xi) SEQUENCE DESCRIPTION: SEQ ID NO: 6:

CCNMGNTGYG GNRWNCCNGA    20

(2) INFORMATION FOR SEQ ID NO: 7:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE:
        (A) DESCRIPTION: cDNA to mRNA (iii) HYPOTHETICAL: no (iv) ANTI-SENSE: yes (ix) FEATURE:
        (D) OTHER INFORMATION: N = other = inosine
            for bases 6, 9 and 11

(xi) SEQUENCE DESCRIPTION:SEQ ID NO: 7:

TTRTGNCCNA NYTCRTG    17

(2) INFORMATION FOR SEQ ID NO: 8:

(i) SEQUENCE CHARACTERISTICS:
        (A) LENGTH: 20 base pairs
        (B) TYPE: nucleic acid
        (C) STRANDEDNESS: double (D) TOPOLOGY: linear (ii) MOLECULE TYPE:
        (A) DESCRIPTION: cDNA to mRNA (iii) HYPOTHETICAL: no (iv) ANTI-SENSE: no (xi) SEQUENCE DESCRIPTION: SEQ ID NO: 8:

TGTCCCGATG GCGAGTGTTT                                           20

(2) INFORMATION FOR SEQ ID NO: 9:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE:
        (A) DESCRIPTION: cDNA to mRNA (iii) HYPOTHETICAL: no (iv) ANTI-SENSE: yes (xi) SEQUENCE DESCRIPTION: SEQ ID NO: 9:

CCTGTTGGCC ATAGTACTGC                                           20

(2) INFORMATION FOR SEQ ID NO: 10:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE:
        (A) DESCRIPTION: cDNA to mRNA (iii) HYPOTHETICAL: no (iv) ANTI-SENSE: no (xi) SEQUENCE DESCRIPTION: SEQ ID NO: 10:

AGATGAATGA GTACACCGTG                                           20

(2) INFORMATION FOR SEQ ID NO: 11:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE:
        (A) DESCRIPTION: cDNA to mRNA (iii) HYPOTHETICAL: no (iv) ANTI-SENSE: yes (xi) SEQUENCE DESCRIPTION: SEQ ID NO: 11:

CCAGTAAGTC CTTGTAAACC                                           20

(2) INFORMATION FOR SEQ ID NO: 12:

(i) SEQUENCE CHARACTERISTICS:
        (A) LENGTH: 20 base pairs
        (B) TYPE: nucleic acid (C) STRANDEDNESS:  double
            (D) TOPOLOGY:  linear (ii) MOLECULE TYPE:
            (A) DESCRIPTION:  cDNA to mRNA (iii) HYPOTHETICAL:  no (iv) ANTI-SENSE:  no (xi) SEQUENCE DESCRIPTION:  SEQ ID NO:  12:

AAGGGACACG AGAGCTGTAT                                                      20

(2) INFORMATION FOR SEQ ID NO:  13:

(i) SEQUENCE CHARACTERISTICS:
            (A) LENGTH:  20 base pairs
            (B) TYPE:  nucleic acid
            (C) STRANDEDNESS:  double
            (D) TOPOLOGY:  linear (ii) MOLECULE TYPE:
            (A) DESCRIPTION:  cDNA to mRNA (iii) HYPOTHETICAL:  no (iv) ANTI-SENSE:  yes (xi) SEQUENCE DESCRIPTION:  SEQ ID NO:  13:

AAGTGGTAGT TGGAGGAAGC                                                      20

(2) INFORMATION FOR SEQ ID NO:  14:

(i) SEQUENCE CHARACTERISTICS:
            (A) LENGTH:  20 base pairs
            (B) TYPE:  nucleic acid
            (C) STRANDEDNESS:  double
            (D) TOPOLOGY:  linear (ii) MOLECULE TYPE:
            (A) DESCRIPTION:  cDNA to mRNA (iii) HYPOTHETICAL:  no (iv) ANTI-SENSE:  no (xi) SEQUENCE DESCRIPTION:  SEQ ID NO:  14:

ATTGGAGAGA GAAAGGCTAC                                                      20

(2) INFORMATION FOR SEQ ID NO:  15:

(i) SEQUENCE CHARACTERISTICS:
            (A) LENGTH:  20 base pairs
            (B) TYPE:  nucleic acid
            (C) STRANDEDNESS:  double
            (D) TOPOLOGY:  linear (ii) MOLECULE TYPE:
            (A) DESCRIPTION:  cDNA to mRNA (iii) HYPOTHETICAL:  no (iv) ANTI-SENSE:  yes (xi) SEQUENCE DESCRIPTION:  SEQ ID NO:  15:

CTTGGGATTG TACTTACAGG                                                      20

(2) INFORMATION FOR SEQ ID NO:  16:

(i) SEQUENCE CHARACTERISTICS:
            (A) LENGTH:  20 base pairs (B) TYPE:  nucleic acid
        (C) STRANDEDNESS:  double
        (D) TOPOLOGY:  linear (ii) MOLECULE TYPE:
        (A) DESCRIPTION:  cDNA to mRNA (iii) HYPOTHETICAL:  no (iv) ANTI-SENSE:  no (xi) SEQUENCE DESCRIPTION: SEQ ID NO:  16:

CTTCCAAAGT GGTCACCTAC                                              20

(2) INFORMATION FOR SEQ ID NO:  17:

(i) SEQUENCE CHARACTERISTICS:
        (A) LENGTH:  20 base pairs
        (B) TYPE:  nucleic acid
        (C) STRANDEDNESS:  double
        (D) TOPOLOGY:  linear (ii) MOLECULE TYPE:
        (A) DESCRIPTION:  cDNA to mRNA (iii) HYPOTHETICAL:  no (iv) ANTI-SENSE:  yes (xi) SEQUENCE DESCRIPTION: SEQ ID NO:  17:

CTAGACTGCT ACCATCCGTC                                              20

(2) INFORMATION FOR SEQ ID NO:  18:

(i) SEQUENCE CHARACTERISTICS:
        (A) LENGTH:  17 base pairs
        (B) TYPE:  nucleic acid
        (C) STRANDEDNESS:  double
        (D) TOPOLOGY:  linear (ii) MOLECULE TYPE:
        (A) DESCRIPTION:  cDNA to mRNA (iii) HYPOTHETICAL:  no (iv) ANTI-SENSE:  no (xi) SEQUENCE DESCRIPTION: SEQ ID NO:  18:

TGCATTGACA ACGAGGC                                                 17

(2) INFORMATION FOR SEQ ID NO:  19:

(i) SEQUENCE CHARACTERISTICS:
        (A) LENGTH:  17 base pairs
        (B) TYPE:  nucleic acid
        (C) STRANDEDNESS:  double
        (D) TOPOLOGY:  linear (ii) MOLECULE TYPE:
        (A) DESCRIPTION:  cDNA to mRNA (iii) HYPOTHETICAL:  no (iv) ANTI-SENSE:  yes (xi) SEQUENCE DESCRIPTION: SEQ ID NO:  19:

CTGTCTTGAC ATTGTTG                                                 17

(2) INFORMATION FOR SEQ ID NO:  20:

(i) SEQUENCE CHARACTERISTICS:

(A) LENGTH:  20 base pairs
        (B) TYPE:  nucleic acid
        (C) STRANDEDNESS:  double
        (D) TOPOLOGY:  linear (ii) MOLECULE TYPE:
        (A) DESCRIPTION:  cDNA to mRNA (iii) HYPOTHETICAL:  no (iv) ANTI-SENSE:  no (xi) SEQUENCE DESCRIPTION: SEQ ID NO:  20:

CTGTGATCCA CCCTGACTAT                                                    20

(2) INFORMATION FOR SEQ ID NO: 21:

(i) SEQUENCE CHARACTERISTICS:
        (A) LENGTH:  20 base pairs
        (B) TYPE:  nucleic acid
        (C) STRANDEDNESS:  double
        (D) TOPOLOGY:  linear (ii) MOLECULE TYPE:
        (A) DESCRIPTION:  cDNA to mRNA (iii) HYPOTHETICAL:  no (iv) ANTI-SENSE:  yes (xi) SEQUENCE DESCRIPTION: SEQ ID NO:  21:

CAGGTGGATG TATGCACACT                                                    20

(2) INFORMATION FOR SEQ ID NO: 22:

(i) SEQUENCE CHARACTERISTICS:
        (A) LENGTH:  20 base pairs
        (B) TYPE:  nucleic acid
        (C) STRANDEDNESS:  double
        (D) TOPOLOGY:  linear (ii) MOLECULE TYPE:
        (A) DESCRIPTION:  cDNA to mRNA (iii) HYPOTHETICAL:  no (iv) ANTI-SENSE:  no (xi) SEQUENCE DESCRIPTION: SEQ ID NO:  22:

GCGCACTGTG TTTATGAGAT                                                    20

(2) INFORMATION FOR SEQ ID NO: 23:

(i) SEQUENCE CHARACTERISTICS:
        (A) LENGTH:  20 base pairs
        (B) TYPE:  nucleic acid
        (C) STRANDEDNESS:  double
        (D) TOPOLOGY:  linear (ii) MOLECULE TYPE:
        (A) DESCRIPTION:  cDNA to mRNA (iii) HYPOTHETICAL:  no (iv) ANTI-SENSE:  yes (xi) SEQUENCE DESCRIPTION: SEQ ID NO:  23:

CTCTTTGGCT TGTACTTGCT                                                    20

(2) INFORMATION FOR SEQ ID NO: 24:

(i) SEQUENCE CHARACTERISTICS:
           (A) LENGTH: 20 base pairs
           (B) TYPE: nucleic acid
           (C) STRANDEDNESS: double
           (D) TOPOLOGY: linear (ii) MOLECULE TYPE:
           (A) DESCRIPTION: cDNA to mRNA (iii) HYPOTHETICAL: no (iv) ANTI-SENSE: no (xi) SEQUENCE DESCRIPTION: SEQ ID NO:    24:

TGAGGGACAT CATTATGCAC                                               20

(2) INFORMATION FOR SEQ ID NO: 25:

(i) SEQUENCE CHARACTERISTICS:
           (A) LENGTH: 20 base pairs
           (B) TYPE: nucleic acid
           (C) STRANDEDNESS: double
           (D) TOPOLOGY: linear (ii) MOLECULE TYPE:
           (A) DESCRIPTION: cDNA to mRNA (iii) HYPOTHETICAL: no (iv) ANTI-SENSE: yes (xi) SEQUENCE DESCRIPTION: SEQ ID NO:    25:

CAAGTTTTCC CCATAATTGG                                               20

(2) INFORMATION FOR SEQ ID NO: 26:

(i) SEQUENCE CHARACTERISTICS:
           (A) LENGTH: 20 base pairs
           (B) TYPE: nucleic acid
           (C) STRANDEDNESS: double
           (D) TOPOLOGY: linear (ii) MOLECULE TYPE:
           (A) DESCRIPTION: cDNA to mRNA (iii) HYPOTHETICAL: no (iv) ANTI-SENSE: no (xi) SEQUENCE DESCRIPTION: SEQ ID NO:    26:

ACAGTACGCC TGGGAGACCA                                               20

(2) INFORMATION FOR SEQ ID NO: 27:

(i) SEQUENCE CHARACTERISTICS:
           (A) LENGTH: 20 base pairs
           (B) TYPE: nucleic acid
           (C) STRANDEDNESS: double
           (D) TOPOLOGY: linear (ii) MOLECULE TYPE:
           (A) DESCRIPTION: cDNA to mRNA (iii) HYPOTHETICAL: no (iv) ANTI-SENSE: yes (xi) SEQUENCE DESCRIPTION: SEQ ID NO:    27:

CTGAGACGGT GCAATTCTGG                                               20

(2) INFORMATION FOR SEQ ID NO:28:

```
    (i) SEQUENCE CHARACTERISTICS:
        (A) LENGTH:  57 amino acids
        (B) TYPE:  amino acid
        (C) STRANDEDNESS:
        (D) TOPOLOGY:  linear (ii) MOLECULE TYPE:
        (A) DESCRIPTION:  protein (iii) HYPOTHETICAL:  no (iv) ANTI-SENSE:  no (v) FRAGMENT TYPE:  internal (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO:   28:

Val Val Thr Ala Ala His Cys Val Tyr Asp Leu Tyr Leu Pro Lys
                  5                  10                  15

Ser Trp Thr Ile Gln Val Gly Leu Val Ser Leu Leu Asp Asn Pro
                 20                  25                  30

Ala Pro Ser His Leu Val Glu Lys Ile Val Tyr His Ser Lys Tyr
                 35                  40                  45

Lys Pro Lys Arg Leu Gly Asn Asp Ile Ala Leu Leu
                 50                  55
```